United States Patent
Hill et al.

(10) Patent No.: US 10,401,738 B2
(45) Date of Patent: Sep. 3, 2019

(54) OVERLAY METROLOGY USING MULTIPLE PARAMETER CONFIGURATIONS

(71) Applicant: KLA-Tencor Corporation, Milpitas, CA (US)

(72) Inventors: Andrew V. Hill, Berkley, CA (US); Andrei V. Shchegrov, Campbell, CA (US); Amnon Manassen, Haifa (IL); Noam Sapiens, Bat Yam (IL)

(73) Assignee: KLA-Tencor Corporation, Milpitas, CA (US)

( * ) Notice: Subject to any disclaimer, the term of this patent is extended or adjusted under 35 U.S.C. 154(b) by 183 days.

(21) Appl. No.: 15/667,401

(22) Filed: Aug. 2, 2017

(65) Prior Publication Data

US 2019/0041329 A1 Feb. 7, 2019

(51) Int. Cl.
| | |
|---|---|
| G02B 3/00 | (2006.01) |
| G03F 7/20 | (2006.01) |
| G01B 11/14 | (2006.01) |
| G01N 21/47 | (2006.01) |
| G01N 21/84 | (2006.01) |
| G02B 27/10 | (2006.01) |
| G02B 27/42 | (2006.01) |

(52) U.S. Cl.
CPC .......... *G03F 7/70633* (2013.01); *G01B 11/14* (2013.01); *G01N 21/4788* (2013.01);
(Continued)

(58) Field of Classification Search
CPC ...... G02B 5/20; G02B 5/203; G02B 27/1013; G02B 27/4205; G02B 27/4211;
(Continued)

(56) References Cited

U.S. PATENT DOCUMENTS

| | | | |
|---|---|---|---|
| 7,047,101 B1* | 5/2006 | Young | G05B 19/41875 382/145 |
| 8,045,786 B2* | 10/2011 | Widmann | G03F 7/70508 359/368 |

(Continued)

FOREIGN PATENT DOCUMENTS

| | | |
|---|---|---|
| WO | 2016162228 A1 | 10/2016 |
| WO | 2017009036 A1 | 1/2017 |

OTHER PUBLICATIONS

U.S. Appl. No. 15/339,312, filed Oct. 31, 2016, Andrew V. Hill et al.

(Continued)

*Primary Examiner* — Gordon J Stock, Jr.
(74) *Attorney, Agent, or Firm* — Suiter Swantz pc llo

(57) ABSTRACT

An overlay metrology system includes an overlay metrology tool configurable to generate overlay signals with a plurality of recipes and further directs an illumination beam to an overlay target and collects radiation emanating from the overlay target in response to the at least a portion of the illumination beam to generate the overlay signal with the particular recipe. The overlay metrology system further acquires two or more overlay signals for a first overlay target using two or more unique recipes, subsequently acquires two or more overlay signals for a second overlay target using the two or more unique recipes, determines candidate overlays for the first and second overlay targets based on the two or more overlay signals for each target, and determines output overlays for the first and second overlay targets based on the two or more candidate overlays for each target.

49 Claims, 10 Drawing Sheets

(52) U.S. Cl.
CPC ....... *G01N 21/4795* (2013.01); *G02B 3/0006* (2013.01); *G02B 27/1013* (2013.01); *G02B 27/4205* (2013.01); *G01N 2021/4709* (2013.01); *G01N 2021/4711* (2013.01); *G01N 2021/8461* (2013.01)

(58) Field of Classification Search
CPC ............ G02B 27/4227; G02B 27/4233; G02B 27/4244; G02B 27/425; G02B 27/4255; G02B 3/0006; G01N 21/47; G01N 21/4788; G01N 21/4795; G01N 2021/4709; G01N 2021/4711; G01N 2021/4714; G01N 2021/4726; G01N 2021/8461; G01N 21/9501; G03F 7/70633; G01B 11/14
USPC ......... 356/399–401; 382/151; 430/5, 22, 30; 355/53, 55, 77; 250/548
See application file for complete search history.

(56) References Cited

U.S. PATENT DOCUMENTS

| | | | | |
|---|---|---|---|---|
| 8,908,147 | B2* | 12/2014 | Den Boef | G03B 27/52 |
| | | | | 355/53 |
| 9,329,033 | B2* | 5/2016 | Amit | G01B 21/042 |
| 9,879,977 | B2* | 1/2018 | Shchegrov | G01B 11/02 |
| 10,018,560 | B2* | 7/2018 | Hill | G02B 27/10 |
| 2008/0094639 | A1 | 4/2008 | Widmann et al. | |
| 2010/0063764 | A1* | 3/2010 | Lou | G05B 19/41875 |
| | | | | 702/94 |
| 2013/0035888 | A1 | 2/2013 | Kandel et al. | |
| 2013/0304408 | A1* | 11/2013 | Pandev | H01L 22/20 |
| | | | | 702/83 |
| 2014/0136137 | A1* | 5/2014 | Tarshish-Shapir | G06T 7/0004 |
| | | | | 702/108 |
| 2016/0290796 | A1 | 10/2016 | Levy et al. | |
| 2016/0313658 | A1 | 10/2016 | Marciano et al. | |
| 2016/0370717 | A1* | 12/2016 | Den Boef | G03F 7/70633 |
| 2017/0219487 | A1 | 8/2017 | Hill | |
| 2017/0350575 | A1* | 12/2017 | Hill | F21V 9/40 |
| 2018/0052099 | A1* | 2/2018 | Hill | G03F 7/70633 |
| 2018/0088470 | A1* | 3/2018 | Bhattacharyya | G03F 7/705 |
| 2018/0292326 | A1* | 10/2018 | Manassen | G01B 11/272 |
| 2019/0004437 | A1* | 1/2019 | Bhattacharyya | G01B 11/272 |

OTHER PUBLICATIONS

U.S. Appl. No. 15/387,180, filed Dec. 21, 2016, Andrew V. Hill et al.

International Search Report and Written Opinion dated Nov. 8, 2018 for PCT/US2018/043606.

* cited by examiner

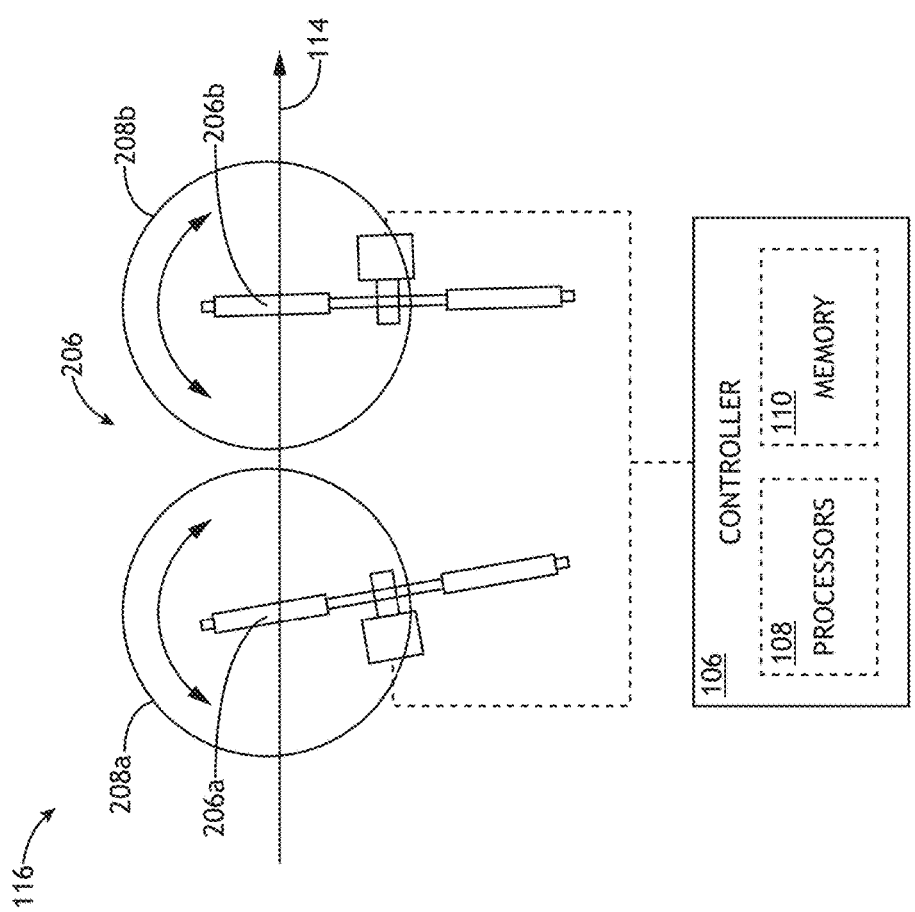

US 10,401,738 B2

OVERLAY METROLOGY USING MULTIPLE PARAMETER CONFIGURATIONS

TECHNICAL FIELD

The present disclosure generally relates to overlay metrology and, more particularly, to overlay metrology with multiple parameter configurations.

BACKGROUND

Overlay metrology systems typically characterize the overlay alignment of multiple layers of a sample by measuring the relative positions of overlay target features located on layers of interest. Further, the overlay alignment of the multiple layers is typically determined by aggregating overlay measurements of multiple overlay targets at various locations across the sample. However, the accuracy and/or repeatability of an overlay measurement of an overlay target may be highly sensitive to variations of process parameters such as, but not limited to thicknesses of film layers. Accordingly, process parameter variations, even those within selected fabrication tolerances, may lead to variations in the accuracy and/or repeatability of overlay measurements across the surface of the sample and thus may negatively impact the overall overlay performance. Therefore, it would be desirable to provide a system and method for curing defects such as those identified above.

SUMMARY

An overlay metrology system is disclosed in accordance with one or more illustrative embodiments of the present disclosure. In one illustrative embodiment, the overlay metrology system includes an overlay metrology tool. In another illustrative embodiment, the overlay metrology tool is configurable to generate overlay signals with a plurality of recipes in which an overlay signal generated with a particular recipe of the plurality of recipes is suitable for determining overlay of two or more layers of a sample and in which the overlay metrology tool directs at least a portion of an illumination beam from an illumination source to an overlay target on the sample and collects radiation emanating from the overlay target in response to the at least a portion of the illumination beam to generate the overlay signal with the particular recipe. In one illustrative embodiment, the overlay metrology system includes a controller communicatively coupled to the overlay metrology tool to sequentially characterize two or more overlay targets on the sample in which characterizing a particular overlay target of the two or more overlay targets includes acquiring two or more overlay signals for the particular overlay target generated with two or more unique recipes from the overlay metrology tool. In another illustrative embodiment, the controller further determines output overlays for the two or more overlay targets in which determining an output overlay for a particular overlay target of the two or more overlay targets includes analyzing the two or more overlay signals for the particular overlay target to generate the output overlay.

An overlay metrology system is disclosed in accordance with one or more illustrative embodiments of the present disclosure. In one illustrative embodiment, the overlay metrology system includes a broadband illumination source to generate an illumination beam. In another illustrative embodiment, the overlay metrology system includes a wavelength selection device to filter the illumination beam to provide a selected wavelength of illumination. In another illustrative embodiment, the overlay metrology system includes an overlay metrology tool. In another illustrative embodiment, the overlay metrology tool is configurable to generate overlay signals with a plurality of recipes including selected wavelengths from the illumination beam provided by the wavelength selection device in which an overlay signal generated with a particular recipe of the plurality of recipes is suitable for determining an overlay measurement for two or more layers of a sample and in which the overlay metrology tool directs illumination from the wavelength selection device to an overlay target on the sample and collects radiation emanating from the overlay target in response to the at least a portion of an illumination beam from an illumination source to generate the overlay signals. In another illustrative embodiment, the overlay metrology system includes a controller communicatively coupled to the wavelength selection device and the overlay metrology tool to sequentially characterize two or more overlay targets on the sample in which characterizing a particular overlay target of the two or more overlay targets includes acquiring two or more overlay signals for the particular overlay target generated with two or more unique recipes from the overlay metrology tool. In another illustrative embodiment, the controller further determines output overlays for the two or more overlay targets in which determining an output overlay for a particular overlay target of the two or more overlay targets includes analyzing the two or more overlay signals for the particular overlay target to generate the output overlay.

An overlay metrology system is disclosed in accordance with one or more illustrative embodiments of the present disclosure. In one illustrative embodiment, the overlay metrology system includes an overlay metrology tool. In another illustrative embodiment, the overlay metrology tool is configurable to generate overlay signals with a plurality of recipes including selected wavelengths from the illumination beam provided by the wavelength selection device in which an overlay signal generated with a particular recipe of the plurality of recipes is suitable for determining an overlay measurement for two or more layers of a sample. In another illustrative embodiment, the overlay metrology tool includes an illumination source to generate an illumination beam including two or more selected wavelengths. In another illustrative embodiment, the overlay metrology tool includes one or more illumination optical elements configured to direct the at least a portion of the illumination beam including the two or more selected wavelengths to the sample. In another illustrative embodiment, the overlay metrology tool includes one or more collection optical elements configured to collect radiation emanating from the sample in response to the at least a portion of the illumination beam including the two or more selected wavelengths. In another illustrative embodiment, the overlay metrology system includes a hyperspectral detector to simultaneously generate two or more overlay signals associated with the radiation emanating from the sample in response to the two or more selected wavelengths. In another illustrative embodiment, the overlay metrology system includes a controller communicatively coupled to the wavelength selection device and the overlay metrology tool to sequentially characterize two or more overlay targets on the sample in which characterizing a particular overlay target of the two or more overlay targets includes acquiring two or more overlay signals for the particular overlay target generated with two or more unique recipes from the overlay metrology tool. In another illustrative embodiment, the controller further determines output overlays for the two or more overlay targets in which determining an output overlay for a particular overlay target of the two or more overlay targets includes analyzing the two or more overlay signals for the particular overlay target to generate the output overlay.

An overlay measurement method is disclosed in accordance with one or more illustrative embodiments of the present disclosure. In one illustrative embodiment, the method includes characterizing two or more overlay targets on the sample sequentially in which characterizing a particular overlay target of the two or more overlay targets includes acquiring two or more overlay signals for the particular overlay target generated with two or more unique recipes from the overlay metrology tool. In another illustrative embodiment, the method includes determining output overlays for the two or more overlay targets in which determining an output overlay for a particular overlay target of the two or more overlay targets includes analyzing the two or more overlay signals for the particular overlay target to generate the output overlay.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which:

FIG. 2B is a conceptual view of a wavelength selection device including angle-tunable spectral filters, in accordance with one or more embodiments of the present disclosure.

DETAILED DESCRIPTION

Figure 1A:
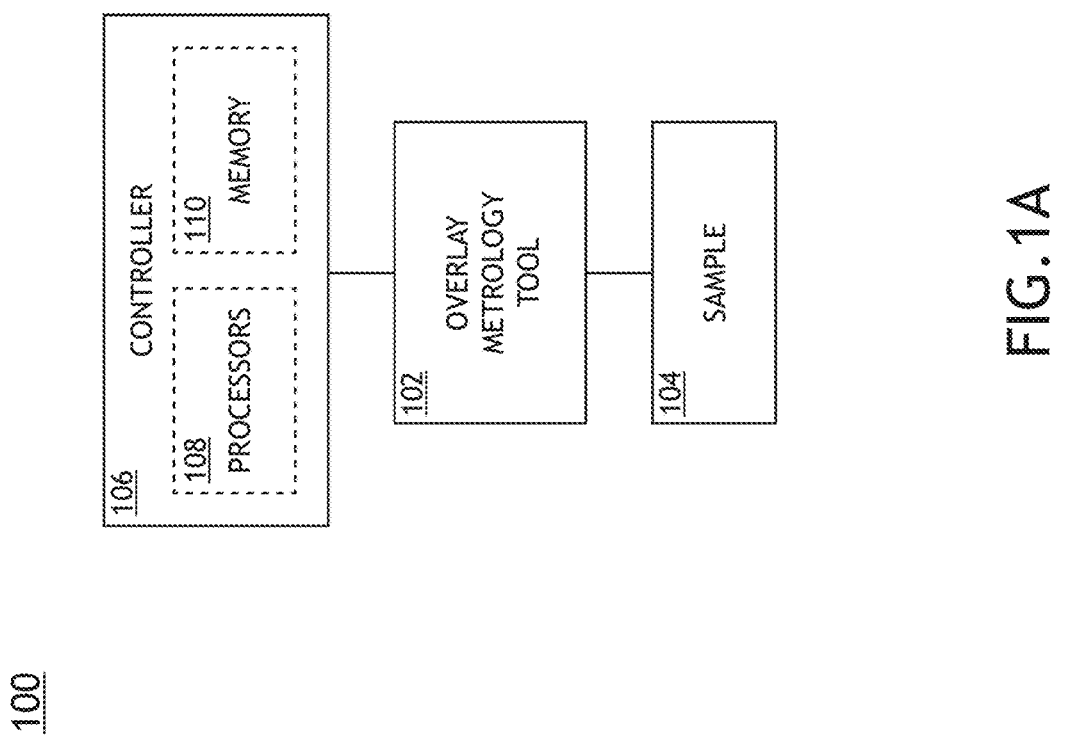
FIG. 1A is a conceptual view illustrating an overlay metrology system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Embodiments of the present disclosure are directed to sequentially analyzing overlay targets on a sample by rapidly acquiring multiple overlay measurements of each overlay target with different recipes of an overlay metrology tool and generating an output overlay for each overlay target based on the multiple overlay measurements. For example, an overlay metrology system may acquire multiple overlay signals with different recipes of an overlay metrology tool for a first overlay target on a sample and may subsequently repeat the process for additional overlay targets on the sample. Each overlay signal associated with a particular recipe may then be used to generate a candidate overlay for the overlay target. The overlay metrology system may then utilize the candidate overlay to generate an output overlay associated with each overlay target. The output overlay may include a single selected candidate overlay providing a desired accuracy or may combine data from the multiple candidate overlay to generate the output overlay with a desired accuracy. In this regard, the multiple candidate overlays acquired at each overlay target on the sample may be utilized to provide a desired overlay accuracy as well as a desired level of repeatability. Additional embodiments of the present disclosure are directed to rapidly tuning recipes of an overlay metrology tool. Accordingly, multiple overlay signals associated with an overlay target may be acquired within a desired timeframe to provide a desired system throughput.

For the purposes of the present disclosure, an overlay signal associated with an overlay metrology tool may be considered to be an output of the overlay metrology tool having sufficient information to determine an overlay including relative positions of overlay target features on two or more sample layers (e.g., through analysis using one or more processors, or the like). For example, an overlay signal may include, but is not required to include, one or more datasets, one or more images, one or more detector readings, or the like.

As used throughout the present disclosure, the term "sample" generally refers to a substrate formed of a semiconductor or non-semiconductor material (e.g., a wafer, or the like). For example, a semiconductor or non-semiconductor material may include, but is not limited to, monocrystalline silicon, gallium arsenide, and indium phosphide. A sample may include one or more layers. For example, such layers may include, but are not limited to, a resist, a dielectric material, a conductive material, and a semiconductive material. Many different types of such layers are known in the art, and the term sample as used herein is intended to encompass a sample on which all types of such layers may be formed. One or more layers formed on a sample may be patterned or unpatterned. For example, a sample may include a plurality of dies, each having repeatable patterned features. Formation and processing of such layers of material may ultimately result in completed devices. Many different types of devices may be formed on a sample, and the term sample as used herein is intended to encompass a sample on which any type of device known in the art is being fabricated. Further, for the purposes of the present disclosure, the term sample and wafer should be interpreted as interchangeable. In addition, for the purposes of the present disclosure, the terms patterning device, mask and reticle should be interpreted as interchangeable.

It is recognized herein that a semiconductor device may be formed as multiple printed layers of patterned material on a substrate. Each printed layer may be fabricated through a series of process steps such as, but not limited to, one or more material deposition steps, one or more lithography steps, or one or more etching steps. Further, each printed layer must typically be fabricated within selected tolerances to properly construct the final device. For example, the relative placement of printed elements in each layer (e.g., the overlay) must be well characterized and controlled with respect to previously fabricated layers. Accordingly, metrology targets may be fabricated on one or more printed layers to enable efficient characterization of the overlay of the layers. Deviations of overlay target features on a printed layer may thus be representative of deviations of printed characteristics of printed device features on that layer. Further, overlay measured at one fabrication step (e.g., after the fabrication of one or more sample layers) may be used to generate correctables for precisely aligning a process tool (e.g., a lithography tool, or the like) for the fabrication of an additional sample layer in a subsequent fabrication step.

Overlay metrology tools may utilize a variety of techniques to determine the overlay of sample layers. For example, image-based overlay metrology tools may illuminate an overlay target (e.g., an advanced imaging metrology (AIM) target, a box-in-box metrology target, or the like) and capture an overlay signal including an image of overlay target features located on different sample layers. Accordingly, overlay may be determined by measuring the relative positions of the overlay target features. By way of another example, scatterometry-based overlay metrology tools may illuminate an overlay target (e.g., a grating-over-grating metrology target, or the like) and capture an overlay signal including an angular distribution of radiation emanating from the overlay target associated with diffraction, scattering, and/or reflection of the illumination beam. Accordingly, overlay may be determined based on models of the interaction of an illumination beam with the overlay target.

Regardless of the overlay measurement technique, an overlay metrology tool is typically configurable according to a recipe including a set of measurement parameters utilized to generate an overlay signal. For example, a recipe of an overlay metrology tool may include, but is not limited to, an illumination wavelength, a detected wavelength of radiation emanating from the sample, a spot size of illumination on the sample, an angle of incident illumination, a polarization of incident illumination, a position of a beam of incident illumination on an overlay target, a position of an overlay target in the focal volume of the overlay metrology tool, or the like. Accordingly, an overlay recipe may include a set of measurement parameters for generating an overlay signal suitable for determining overlay of two or more sample layers.

The accuracy and/or the repeatability of an overlay measurement may depend on the overlay recipe as well as a wide range of factors associated with the particular geometry of the overlay target such as, but not limited to, thicknesses of sample layers, the sizes of overlay target features, the density or pitch of overlay target features, or the composition of sample layers. Further, the particular geometry of overlay targets may vary across the sample in both predictable and unpredictable manners. For example, the thicknesses of fabricated layers may vary across the sample in a known distribution (e.g., a thickness may be expected to be slightly larger in the center of a sample than along an edge) or may vary according to random fluctuations associated with defects or random variations of processing steps. Accordingly, a particular overlay recipe may not provide the same accuracy and/or repeatability when applied to all overlay targets of a sample, even if process variations are within selected fabrication tolerances.

Embodiments of the present disclosure are directed to acquiring multiple overlay signals for overlay targets on a sample with multiple recipes. The multiple overlay signals may then be utilized to generate multiple candidate overlays. Further, an output overlay (e.g., a determination of relative positions of sample layers) may be determined based on the multiple candidate overlays. In this regard, an overlay measurement system may be robust to process variations and may flexibly determine overlay at each overlay target with desired performance characteristics. Accordingly, accurate correctables for a process tool for precisely fabricating a subsequent sample layer may be generated based on the robust and accurate overlay determined for each overlay target.

Additional embodiments of the present disclosure are directed to sequentially analyzing overlay targets on a sample by aligning the sample for characterization of a particular overlay target, acquiring multiple overlay signals for the particular overlay target with different recipes, and subsequently aligning the sample for characterization of an additional overlay target and repeating the process. In one embodiment, the multiple acquired overlay signals for each overlay target are analyzed to determine an overlay for the overlay target in real time. In another embodiment, the multiple acquired overlay signals for each overlay target are analyzed to determine an overlay for the overlay target in a subsequent process step. For example, the multiple acquired overlay signals for each overlay target may be stored (e.g., in a memory of a processing device) for subsequent analysis.

Additional embodiments of the present disclosure are directed to rapidly tuning system parameters of an overlay metrology tool to provide rapid overlay signal acquisitions with different overlay recipes. It is recognized herein that acquiring multiple overlay signals for overlay targets in a single sample alignment within the overlay metrology tool may provide for efficient overlay determination with a high level of repeatability. For example, a field of view of an overlay metrology tool may typically be on the order of the size of an overlay target to provide high resolution of the overlay target and/or to precisely position an illumination beam on the overlay target. Accordingly, a sample containing multiple overlay targets must typically be translated to align the overlay metrology tool to a particular overlay target. In some applications, sample translation and alignment may be relatively time-consuming with respect to the acquisition of an overlay signal and may thus present a bottleneck in system throughput. In this regard, acquiring multiple overlay signals for overlay targets in a single sample alignment within the overlay metrology tool may facilitate high measurement accuracy while maintaining a selected level of throughput.

FIG. 1A is a conceptual view illustrating an overlay metrology system 100, in accordance with one or more embodiments of the present disclosure.

In one embodiment, the overlay metrology system 100 includes an overlay metrology tool 102 to acquire overlay signals from overlay targets based on any number of overlay recipes. For example, the overlay metrology tool 102 may direct illumination to a sample 104 and may further collect radiation emanating from the sample 104 to generate an overlay signal suitable for the determination of overlay of two or more sample layers. The overlay metrology tool 102 may be any type of overlay metrology tool known in the art suitable for generating overlay signals suitable for determining overlay associated with overlay targets on a sample 104. The overlay metrology tool 102 may operate in an imaging mode or a non-imaging mode. For example, in an imaging mode, individual overlay target elements may be resolvable within the illuminated spot on the sample (e.g., as part of a bright-field image, a dark-field image, a phase-contrast image, or the like). By way of another example, the overlay metrology tool 102 may operate as a scatterometry-based overlay metrology tool in which radiation from the sample is analyzed at a pupil plane to characterize the angular distribution of radiation from the sample 104 (e.g., associated with scattering and/or diffraction of radiation by the sample 104).

Further, the overlay tool may be configurable to generate overlay signals based on any number of recipes defining measurement parameters for acquiring an overlay signal suitable for determining overlay of an overlay target. For example, a recipe of an overlay metrology tool may include, but is not limited to, an illumination wavelength, a detected wavelength of radiation emanating from the sample, a spot size of illumination on the sample, an angle of incident illumination, a polarization of incident illumination, a position of a beam of incident illumination on an overlay target, a position of an overlay target in the focal volume of the overlay metrology tool, or the like.

In another embodiment, the overlay metrology system 100 includes a controller 106 communicatively coupled to the overlay metrology tool 102. The controller 106 may be configured to direct the overlay metrology tool 102 to generate overlay signals based on one or more selected recipes. The controller 106 may be further configured to receive data including, but not limited to, overlay signals from the overlay metrology tool 102. Additionally, the controller 106 may be configured to determine overlay associated with an overlay target based on the acquired overlay signals.

In another embodiment, the controller 106 includes one or more processors 108. For example, the one or more processors 108 may be configured to execute a set of program instructions maintained in a memory device 110, or memory. The one or more processors 108 of a controller 106 may include any processing element known in the art. In this sense, the one or more processors 108 may include any microprocessor-type device configured to execute algorithms and/or instructions. Further, the memory device 110 may include any storage medium known in the art suitable for storing program instructions executable by the associated one or more processors 108. For example, the memory device 110 may include a non-transitory memory medium. As an additional example, the memory device 110 may include, but is not limited to, a read-only memory, a random access memory, a magnetic or optical memory device (e.g., disk), a magnetic tape, a solid state drive and the like. It is further noted that memory device 110 may be housed in a common controller housing with the one or more processors 108.

Figure 1B:
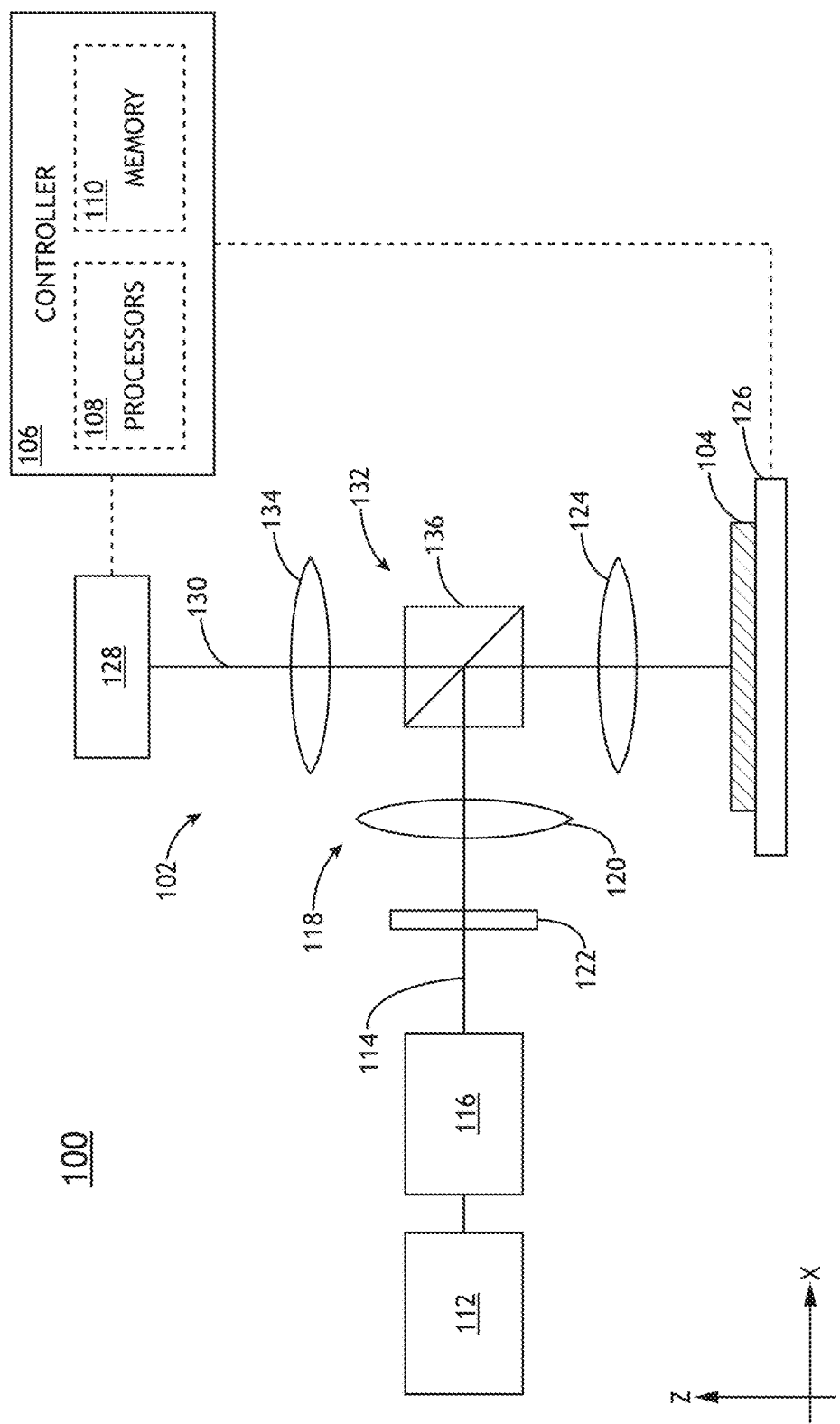
FIG. 1B is a conceptual view illustrating the overlay metrology tool, in accordance with one or more embodiments of the present disclosure.

FIG. 1B is a conceptual view illustrating the overlay metrology tool 102, in accordance with one or more embodiments of the present disclosure. In one embodiment, the overlay metrology tool 102 includes an illumination source 112 configured to generate an illumination beam 114. The illumination beam 114 may include one or more selected wavelengths of light including, but not limited to, ultraviolet (UV) radiation, visible radiation, or infrared (IR) radiation.

The illumination source 112 may include any type of illumination source suitable for providing an illumination beam 114. In one embodiment, the illumination source 112 is a laser source. For example, the illumination source 112 may include, but is not limited to, one or more narrowband laser sources, a broadband laser source, a supercontinuum laser source, a white light laser source, or the like. In this regard, the illumination source 112 may provide an illumination beam 114 having high coherence (e.g., high spatial coherence and/or temporal coherence). In another embodiment, the illumination source 112 includes a laser-sustained plasma (LSP) source. For example, the illumination source 112 may include, but is not limited to, a LSP lamp, a LSP bulb, or a LSP chamber suitable for containing one or more elements that, when excited by a laser source into a plasma state, may emit broadband illumination. In another embodiment, the illumination source 112 includes a lamp source. For example, the illumination source 112 may include, but is not limited to, an arc lamp, a discharge lamp, an electrodeless lamp, or the like. In this regard, the illumination source 112 may provide an illumination beam 114 having low coherence (e.g., low spatial coherence and/or temporal coherence).

In another embodiment, the overlay metrology system 100 includes a wavelength selection device 116 to control the spectrum of the illumination beam 114 for illumination of the sample 104. For example, the wavelength selection device 116 may include a tunable filter suitable for providing an illumination beam 114 with a selected spectrum (e.g., center wavelength, bandwidth, spectral profile, or the like). By way of another example, the wavelength selection device 116 may adjust one or more control settings of a tunable illumination source 112 to directly control the spectrum of the illumination beam 114. Further, the controller 106 may be communicatively coupled to the illumination source 112 and/or the wavelength selection device 116 to adjust one or more aspects of the spectrum of the illumination beam 114.

In another embodiment, the overlay metrology tool 102 directs the illumination beam 114 to the sample 104 via an illumination pathway 118. The illumination pathway 118 may include one or more optical components suitable for modifying and/or conditioning the illumination beam 114 as well as directing the illumination beam 114 to the sample 104. For example, the illumination pathway 118 may include, but is not required to include, one or more lenses 120 (e.g., to collimate the illumination beam 114, to relay pupil and/or field planes, or the like), one or more polarizers 122 to adjust the polarization of the illumination beam 114, one or more filters, one or more beam splitters, one or more diffusers, one or more homogenizers, one or more apodizers, one or more beam shapers, or one or more mirrors (e.g., static mirrors, translatable mirrors, scanning mirrors, or the like). In another embodiment, the overlay metrology tool 102 includes an objective lens 124 to focus the illumination beam 114 onto the sample 104 (e.g., an overlay target with overlay target elements located on two or more layers of the sample 104). In another embodiment, the sample 104 is disposed on a sample stage 126 suitable for securing the sample 104 and further configured to position the sample 104 with respect to the illumination beam 114.

In another embodiment, the overlay metrology tool 102 includes one or more detectors 128 configured to capture radiation emanating from the sample 104 (e.g., an overlay target on the sample 104) (e.g., sample radiation 130) through a collection pathway 132 and generate one or more overlay signals indicative of overlay of two or more layers of the sample 104. The collection pathway 132 may include multiple optical elements to direct and/or modify illumination collected by the objective lens 124 including, but not limited to one or more lenses 134, one or more filters, one or more polarizers, one or more beam blocks, or one or more beamsplitters. For example, a detector 128 may receive an image of the sample 104 provided by elements in the collection pathway 132 (e.g., the objective lens 124, the one or more lenses 134, or the like). By way of another example, a detector 128 may receive radiation reflected or scattered (e.g., via specular reflection, diffuse reflection, and the like) from the sample 104. By way of another example, a detector 128 may receive radiation generated by the sample (e.g., luminescence associated with absorption of the illumination beam 114, and the like). By way of another example, a detector 128 may receive one or more diffracted orders of radiation from the sample 104 (e.g., 0-order diffraction, ±1 order diffraction, ±2 order diffraction, and the like).

The illumination pathway 118 and the collection pathway 132 of the overlay metrology tool 102 may be oriented in a wide range of configurations suitable for illuminating the sample 104 with the illumination beam 114 and collecting radiation emanating from the sample 104 in response to the incident illumination beam 114. For example, as illustrated in FIG. 1B, the overlay metrology tool 102 may include a beamsplitter 136 oriented such that the objective lens 124 may simultaneously direct the illumination beam 114 to the sample 104 and collect radiation emanating from the sample 104. By way of another example, the illumination pathway 118 and the collection pathway 132 may contain non-overlapping optical paths.

Figure 1C:
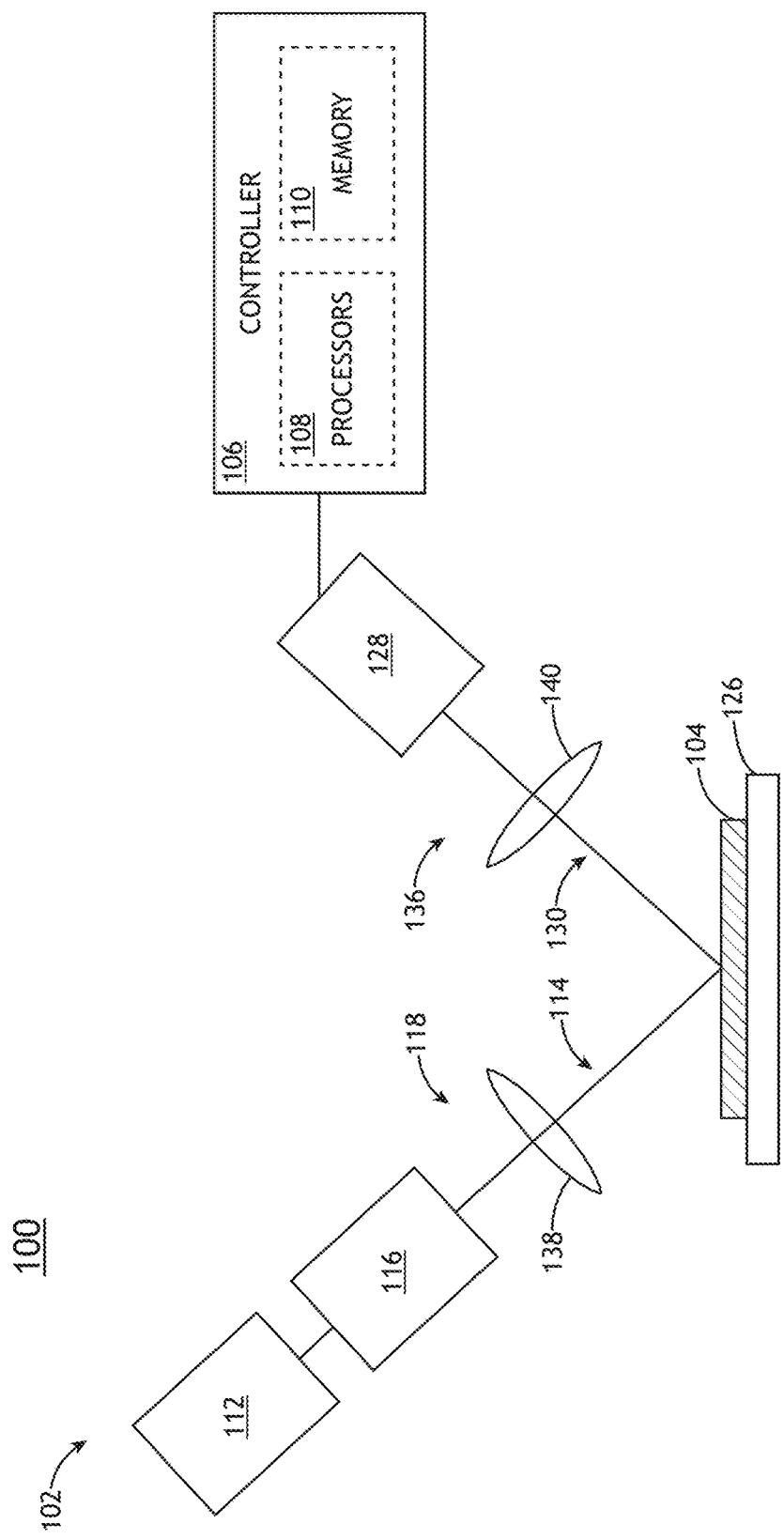
FIG. 1C is a conceptual view illustrating an overlay metrology tool, in accordance with one or more embodiments of the present disclosure.

FIG. 1C is a conceptual view illustrating an overlay metrology tool 102, in accordance with one or more embodiments of the present disclosure. In one embodiment, the illumination pathway 118 and the collection pathway 132 contain separate elements. For example, the illumination pathway 118 may utilize a first focusing element 138 to focus the illumination beam 114 onto the sample 104 and the collection pathway 132 may utilize a second focusing element 140 to collect radiation from the sample 104. In this regard, the numerical apertures of the first focusing element 138 and the second focusing element 140 may be different. In another embodiment, one or more optical components may be mounted to a rotatable arm (not shown) pivoting around the sample 104 such that the angle of incidence of the illumination beam 114 on the sample 104 may be controlled by the position of the rotatable arm.

As described previously herein, the overlay metrology tool 102 may be configurable to generate overlay signals associated with overlay targets on the sample 104 using any number of overlay recipes (e.g., sets of measurement parameters). Further, the overlay metrology tool 102 may provide rapid tuning of the measurement parameters such that multiple overlay signals based on different recipes may be rapidly acquired. For example, the controller 106 of the overlay metrology system 100 may be communicatively coupled with one or more adjustable components of the overlay metrology tool 102 to configure the adjustable components in accordance with an overlay recipe.

An overlay recipe may include one or more aspects of the spectrum of the illumination beam 114 incident on the sample such as, but not limited to the wavelength (e.g., the central wavelength), the bandwidth, and the spectral profile of the illumination beam 114 as measurement parameters. For example, the controller 106 may be communicatively coupled to the illumination source 112 and/or the wavelength selection device 116 to adjust the spectrum of the illumination beam 114 in accordance with an overlay recipe.

In one embodiment, the wavelength selection device 116 includes one or more position-tunable spectral filters in which spectral characteristics of an incident illumination beam 114 (e.g., a center wavelength, a bandwidth, a spectral transmissivity value or the like) may be rapidly tuned by modifying the position of the illumination beam 114 on the filter. Further, position-tunable spectral filters may include any type of spectral filter such as, but not limited to, a low-pass filter, a high-pass filter, a band-pass filter, or a band-reject filter.

For example, a position-tunable spectral filter may include one or more thin films operating as an edge filter with a position-tunable cutoff wavelength. In this regard, the cutoff wavelength may be tuned by modifying the position of the illumination beam 114 on the filter. For instance, a low-pass edge filter may pass (e.g., via transmission or reflection) wavelengths below the cutoff wavelength, whereas a high-pass edge filter may pass wavelengths above the cutoff wavelength. Further, a band-pass filter may be formed from a low-pass edge filter combined with a high-pass edge filter.

Figure 2A:
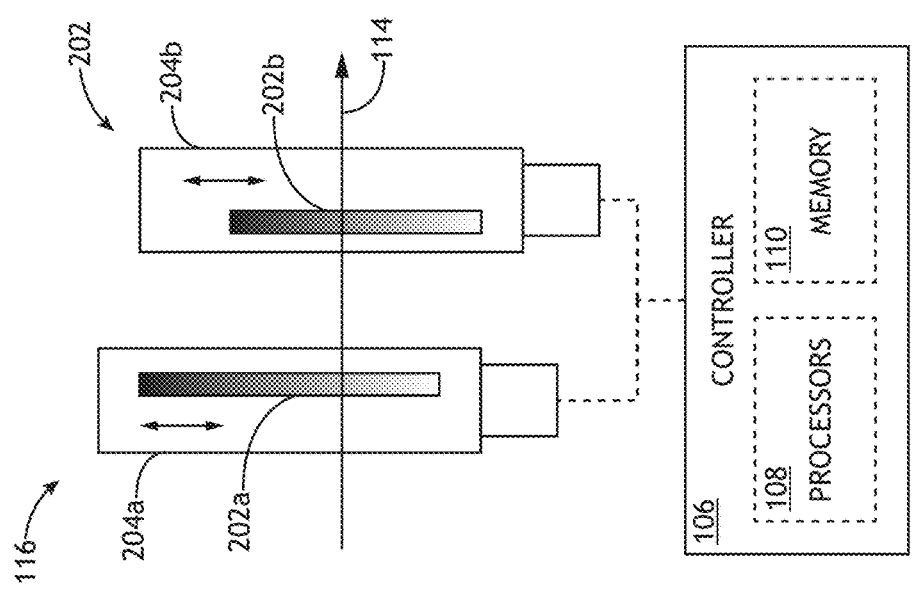
FIG. 2A is a conceptual view of a wavelength selection device including position-tunable spectral filters, in accordance with one or more embodiments of the present disclosure.

FIG. 2A is a conceptual view of a wavelength selection device 116 including position-tunable spectral filters, in accordance with one or more embodiments of the present disclosure. In one embodiment, the wavelength selection device 116 includes one or more position-tunable spectral filters 202 secured to one or more linear translation stages 204 (e.g., via single filter mounts, filter wheels, or the like) positioned to filter the spectrum of the illumination beam 114 from the illumination source 112 (e.g., configured as a broadband illumination source). Further, the linear translation stages 204 may be communicatively coupled to the controller 106 such that the position of the illumination beam 114 on the position-tunable spectral filters 202 may be adjusted.

In another embodiment, as illustrated in FIG. 2A, a first position-tunable spectral filter 202*a* is mounted on a first linear translation stage 204*a* includes a low-pass edge filter with a position-tunable cutoff wavelength. Additionally, a second position-tunable spectral filter 202*b* is mounted on a second linear translation stage 204*b* includes a high-pass edge filter with a position-tunable cutoff wavelength. Further, the first linear translation stage 204*a* and the second linear translation stage 204*b* may be independently adjustable. Accordingly, the positions of the first position-tunable spectral filter 202*a* and the second position-tunable spectral filter 202*b* may together define the spectral characteristics of the transmitted illumination beam 114.

The speed at which a position-tunable filter may tune the spectral characteristics of an incident illumination beam 114 may be governed by the translation speed of the illumination beam 114 across the filter. For example, the tuning speed may be governed by the translation speeds of the first position-tunable spectral filter 202*a* and the second position-tunable spectral filter 202*b* of FIG. 2A. In another embodiment, though not shown, the overlay metrology tool 102 includes a beam-scanning device (e.g., one or more linearly translatable mirrors, one or more galvo mirrors, or the like) communicatively coupled with the controller 106 to modify the position of the illumination beam 114 on one or more position-tunable filters. Accordingly, the tuning speed may be governed by the scanning speed of the beam-scanning device.

In another embodiment, the wavelength selection device 116 includes one or more angle-tunable spectral filters in which spectral characteristics of an incident illumination beam 114 (e.g., a center wavelength, a bandwidth, a spectral transmissivity value or the like) may be rapidly tuned by modifying the angle of the illumination beam 114 on the filter. Further, angle-tunable spectral filters may include any type of spectral filter such as, but not limited to, a low-pass filter, a high-pass filter, a band-pass filter, or a band-reject filter. For example, an angle-tunable spectral filter may include one or more thin films operating as an edge filter with a position-tunable cutoff wavelength. In this regard, the cutoff wavelength may be tuned by modifying the angle of the illumination beam 114 on the filter.

FIG. 2B is a conceptual view of a wavelength selection device 116 including angle-tunable spectral filters, in accordance with one or more embodiments of the present disclosure. In one embodiment, the wavelength selection device 116 includes one or more angle-tunable spectral filters 206 secured to one or more rotational translation stages 208 (e.g., via single filter mounts, filter wheels, or the like) positioned to filter the spectrum of the illumination beam 114 from the illumination source 112 (e.g., configured as a broadband illumination source). Further, the rotational translation stages 208 may be communicatively coupled to the controller 106 such that the angle of the illumination beam 114 on the angle-tunable spectral filters 206 may be adjusted.

In another embodiment, as illustrated in FIG. 2B, a first angle-tunable spectral filter 206a is mounted on a first rotational translation stage 208a that includes a low-pass edge filter with a position-tunable cutoff wavelength. Additionally, a second angle-tunable spectral filter 206b is mounted on a second rotational translation stage 208b that includes a high-pass edge filter with a position-tunable cutoff wavelength. Further, the first rotational translation stage 208a and the second rotational translation stage 208b may be independently adjustable. Accordingly, the positions of the first angle-tunables pectral filter 206a and the second angle-tunable spectral filter 206b may together define the spectral characteristics of the transmitted illumination beam 114.

The speed at which an angle-tunable filter may tune the spectral characteristics of an incident illumination beam 114 may be governed by the translation speed of the angle of the illumination beam 114 on the filter. For example, the tuning speed may be governed by the translation speeds of the first angle-tunable spectral filter 206a and the second angle-tunable spectral filter 206b of FIG. 2B. In another embodiment, though not shown, the overlay metrology tool 102 includes a beam-scanning device (e.g., one or more linearly translatable mirrors, one or more galvo mirrors, or the like) communicatively coupled with the controller 106 to modify the angle of the illumination beam 114 on one or more angle-tunable filters. Accordingly, the tuning speed may be governed by the scanning speed of the beam-scanning device.

In another embodiment, the wavelength selection device 116 includes a double monochromator including one or more dynamically-adjustable diffraction gratings coupled to a spatial filter to provide rapid tuning of the spectral characteristics of the illumination beam 114. Dynamically-adjustable diffraction gratings coupled with spatial filters to provide spectral filtering of an incident beam is generally described in U.S. patent application Ser. No. 15/339,312, titled "System and Method for Spectral Tuning of Broadband Light Sources" and filed on Oct. 31, 2016, which is incorporated herein by reference in its entirety. A dynamically generated grating may provide spectral tuning of the illumination beam 114 without physically moving components (e.g., translation stages, translatable mirrors, galvo mirrors, or the like). Accordingly, a wavelength selection device 116 including a dynamically-generated grating may facilitate highly-repeatable spectral tuning at high speeds suitable for rapid acquisition of overlay signals with different wavelengths.

Figure 2C:
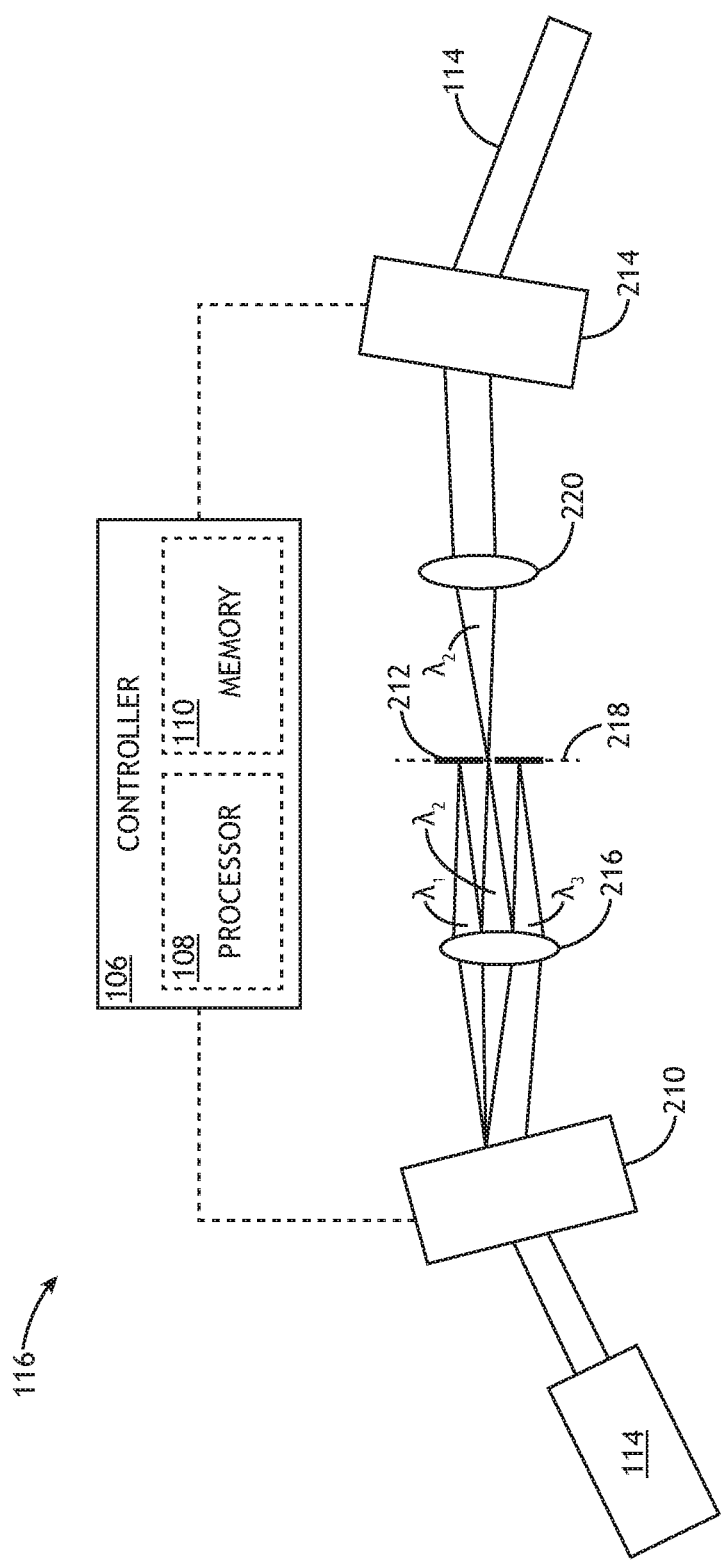
FIG. 2C is a conceptual view of a wavelength selection device including a double-grating monochromator with a spatial filter, in accordance with one or more embodiments of the present disclosure.

FIG. 2C is a conceptual view of a wavelength selection device 116 including a double-grating monochromator with a spatial filter, in accordance with one or more embodiments of the present disclosure. In one embodiment, the wavelength selection device 116 includes a first dispersive element 210 to spectrally disperse the illumination beam 114, a filtering element 212 to operate as a spatial filter, and a second dispersive element 214 to spectrally recombine the dispersed illumination beam 114 to form a spectrally-filtered illumination beam 114. In this regard, the second dispersive element 214 may remove the dispersion introduced by the first dispersive element 210. Further, a spectral transmittance of the wavelength selection device 116 may be related to a spatial transmittance of the filtering element 212.

The first dispersive element 210 may be any type of dispersive element known in the art suitable for introducing spectral dispersion into the illumination beam 114. For example, the first dispersive element 210 may introduce dispersion into the illumination beam 114 through any mechanism such as, but not limited to, diffraction or refraction. Further, the first dispersive element 210 may be formed from transmissive and/or reflective optical elements.

In another embodiment, the first dispersive element 210 includes a dynamically-generated diffraction grating. In this regard, a diffraction grating may be dynamically generated in a substrate material (e.g., a transparent optical material). Further, the dispersive characteristics of the first dispersive element 210 may be dynamically modified in order to tune the wavelength selection device 116 by adjusting the physical characteristics of the dynamically-generated diffraction grating. For example, the period or the modulation depth of a dynamically-generated diffraction grating may be adjusted (e.g., via the controller 106) to control the value of dispersion (e.g., the angles at which particular wavelengths of illumination are diffracted). By way of another example, the modulation depth of the dynamically-generated diffraction grating may be adjusted (e.g., via the controller 106) to control the efficiency of dispersion (e.g., an efficiency value at which particular wavelengths of illumination are diffracted).

For example, the first dispersive element 210 may include, but is not limited to, an acousto-optic deflector on an electro-optic modulator. It is noted herein that a wavelength selection device 116 including a double grating monochromator with an acousto-optic deflector may provide fast tuning of a spatially coherent illumination beam 114 (e.g., generated by a supercontinuum laser source, or the like). In one embodiment, the first dispersive element 210 includes an acousto-optic deflector consisting of a solid medium coupled with a transducer configured to generate ultrasonic waves that propagate through the solid medium. Properties of the solid medium such as, but not limited to, the refractive index may be modified by the propagating ultrasonic waves such that an illumination beam 114 is diffracted upon interaction with the solid medium. Furthermore, ultrasonic waves may propagate through the solid medium at the velocity of sound in the medium and have a wavelength related to the frequency of the drive signal as well as the velocity of sound in the solid medium. Accordingly, a modulation frequency and/or a modulation strength of a transducer may be dynamically adjusted to modify the physical characteristics of the dynamically-generated diffraction grating and the corresponding dispersive properties of the first dispersive element 210.

In another embodiment, the wavelength selection device 116 includes a first optical element 216 (e.g., one or more lenses, or the like) to focus the spectrally-dispersed illumination beam 114 to a focal plane 218 such that the spectrum of the illumination beam 114 may be spatially distributed across the focal plane 218. Accordingly, the focal plane 218 may correspond to a diffraction plane of the wavelength selection device 116. In this regard, a "position" within the focal plane 218 may correspond to light from the illumination beam 114 exiting the first dispersive element 210 at a particular angle and thus a particular wavelength of illumination of the illumination beam 114. For example, a first dispersive element 210 including a diffraction grating may diffract each wavelength of illumination of the illumination beam 114 at a different angle, whereupon each wavelength of illumination of the illumination beam 114 may be focused to a different location in the focal plane 218.

In another embodiment, the filtering element 212 of the wavelength selection device 116 is located at the focal plane 218. In this regard, the filtering element 212 may spatially filter the spectrally-dispersed illumination beam 114. For example, the filtering element 212 may have a spatial transmittance describing the transmittance of illumination (e.g., illumination of any wavelength) as a function of position. Accordingly, the spectral power of each wavelength of the illumination beam 114 may be modified according to the spatial transmittance of the filtering element 212. In this regard, the spectral transmittance of the wavelength selection device 116 may be controllable through the spatial transmittance of the filtering element 212. In one instance, the filtering element 212 may pass a select wavelength (or wavelength range) of the illumination beam 114.

In another embodiment, the wavelength selection device 116 includes a second optical element 220 (e.g., one or more lenses, or the like) to collect the spectrally-dispersed illumination passed by the filtering element 212. For example, the second optical element 220 may collect at least a portion of the spectrally dispersed and filtered illumination beam 114 from the filtering element 212. Further, the second optical element 220 may direct the collected spectrally dispersed and filtered illumination beam 114 to the second dispersive element 214.

In another embodiment, the second dispersive element 214 spectrally combines the spectrally dispersed and filtered illumination beam 114 to remove the spectral dispersion introduced by the first dispersive element 210. In this regard, an illumination beam 114 exiting the second dispersive element 214 may be a spectrally-filtered version of the input illumination beam 114. For example, the dispersive characteristics of the second optical element 220 may be configured to counteract the dispersion induced by the first dispersive element 210.

In another embodiment, the first optical element 216 and the second optical element 220 form an optical relay system. In this regard, the first optical element 216 and the second optical element 220 may generate an image of the distribution of the illumination beam 114 on the first dispersive element 210 at the second dispersive element 214. Accordingly, the wavelength selection device 116 may minimally affect the properties of the illumination beam 114 such as, but not limited to, the divergence (e.g., degree of collimation), spatial coherence, or brightness (e.g., of the passed wavelengths), which may facilitate the integration of the wavelength selection device 116 into the overlay metrology tool 102.

In another embodiment, the wavelength selection device 116 includes a multi-channel spectral filter to provide rapid tuning of the spectral characteristics of the illumination beam 114. A multi-channel spectral filter is generally described in U.S. patent application Ser. No. 15/387,180, titled "System and Method for Generating Multi-Channel Tunable Illumination from a Broadband Source" and filed on Dec. 21, 2016, which is incorporated herein by reference in its entirety. For example, a multi-channel spectral filter may include two or more channels with fixed spectral transmissivities (e.g., fixed spectral filtering characteristics) and a channel selector to route an incident beam (e.g., the illumination beam 114) to one or more channels. Accordingly, the spectral characteristics of an input illumination beam 114 may be rapidly tuned between multiple-predefined spectral distributions (e.g., center wavelengths, bandwidths, spectral profiles, or the like) by modifying which channel(s) the illumination beam 114 is routed through. Accordingly, a multi-channel spectral filter may provide rapid switching between fixed spectral characteristics (e.g., associated with different overlay recipes) without requiring dynamic spectral tuning. Further, the switching speed may be governed by the switching speed of the channel selector.

Figure 2D:
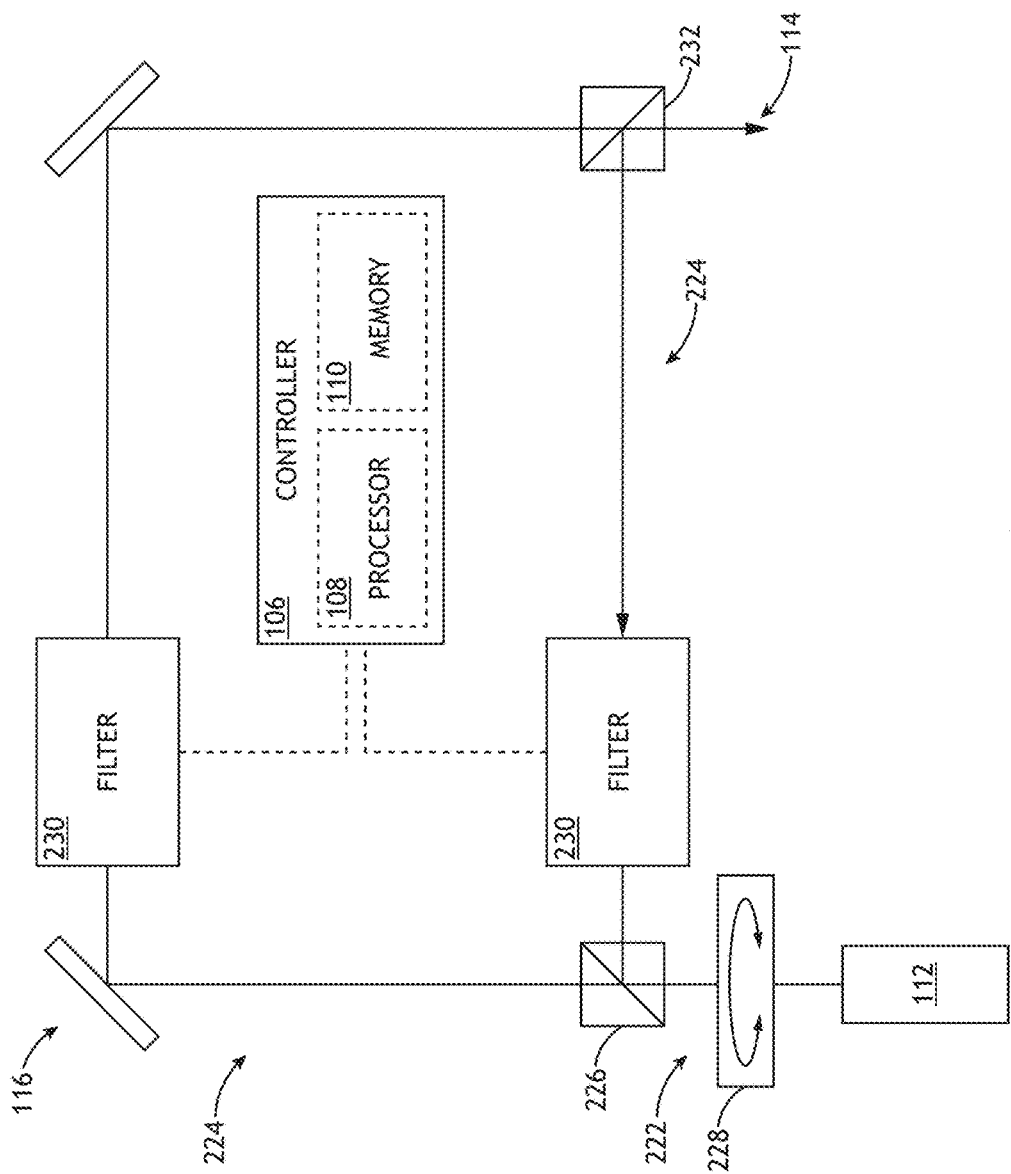
FIG. 2D is a conceptual view of a wavelength selection device including a multi-channel spectral filter, in accordance with one or more embodiments of the present disclosure.

FIG. 2D is a conceptual view of a wavelength selection device 116 including a multi-channel spectral filter, in accordance with one or more embodiments of the present disclosure. In one embodiment, the wavelength selection device 116 includes a channel selector 222 to separate the illumination beam 114 into two or more channel beams 224 (e.g., portions of the illumination beam propagating along any of the two or more filtering channels). The channel selector 222 may be any optical element or combination of elements suitable for selectably directing the incident illumination beam 114 into one or more filtering channels. For example, the channel selector 222 may include, but is not limited to, one or more beamsplitters 226, one or more polarization rotators 228, one or more dichroic mirrors, or one or more beam-routing elements (e.g., translatable mirrors, galvo mirrors, or the like). In another embodiment, the controller 106 is communicatively coupled to the channel selector 222 to direct to the channel selector 222 to provide the illumination beam 114 with selected spectral properties.

In another embodiment, each filtering channel of the wavelength selection device 116 includes a filter 230 to control the spectral content of the channel beam 224. The filter 230 may include any type of filter suitable for modifying the spectral content of the illumination beam 114 such as, but not limited to, static spectral filters (e.g., dielectric filters, metallic filters, or the like) having fixed spectral transmissivities, tunable spectral filters (e.g., position-tunable spectral filters, angle-tunable spectral filters, or acousto-optic double monochromators as described previously herein).

In another embodiment, the wavelength selection device 116 includes a beam combiner 232 to combine the paths of each of the filtering channels. In this regard, the path of the filtered illumination beam 114 provided as an output by the wavelength selection device 116 may be the same regardless of the filtering channel used.

In some embodiments, the overlay metrology tool 102 may simultaneously illuminate the sample 104 (e.g., an overlay target on the sample 104) with multiple wavelengths of illumination in which each wavelength may correspond to a different overlay recipe. The overlay metrology tool 102 may then detect radiation emanating from the sample 104 in response to each wavelength to simultaneously generate multiple overlay signals associated with the different overlay recipes. For example, the overlay metrology tool 102 may include a spectrometer and/or a hyperspectral detection system as part of the collection pathway 132 to separately and simultaneously detect radiation emanating from the sample 104 associated with different incident wavelengths. In this regard, the time required to capture the multiple overlay signals associated with the different overlay recipes may be governed by the total acquisition time of the spectrometer and/or the hyperspectral detection system (e.g., the acquisition time of a detector 128 of a hyperspectral detection system).

Simultaneous capture of pupil planes of a metrology tool using a hyperspectral system is generally described in U.S. patent application Ser. No. 15/233,648, titled "System and Method for Hyperspectral Imaging Metrology" and filed on Aug. 10, 2016, which is incorporated herein by reference in its entirety. For example, a hyperspectral imaging sub-system may spectrally disperse radiation emanating from the sample 104 (e.g., an overlay target on the sample 104) at a pupil plane, divide the pupil plane into multiple segments, and direct the radiation associated with each segment to spatially separated portions of a detector. In this regard, illumination associated with the pupil plane may be segmented and distributed as a spectrally-dispersed array pattern on the detector. Accordingly, illumination associated with the pupil plane having different wavelengths may occupy different locations on the detector.

Figure 3:
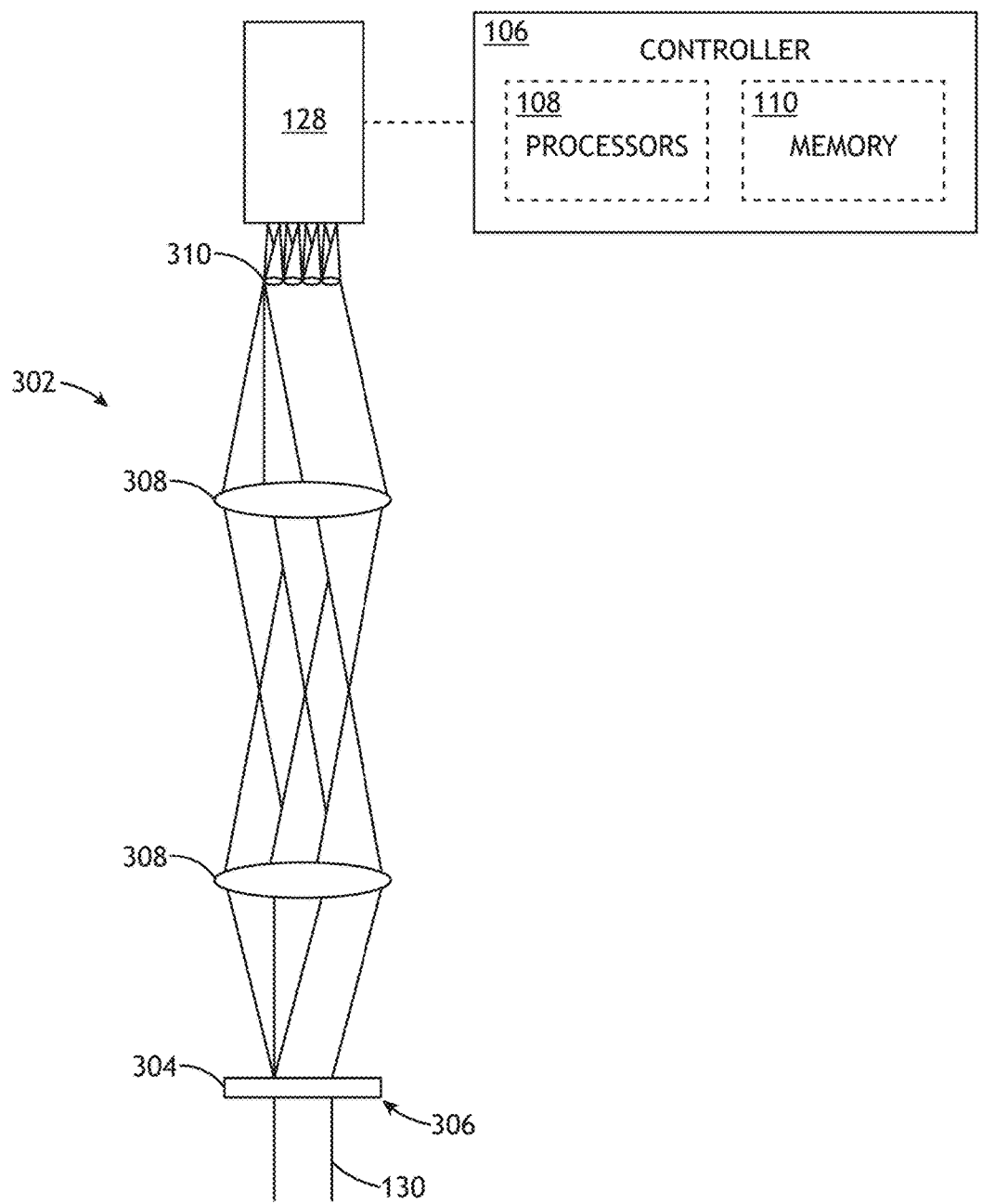
FIG. 3 is a conceptual view of a hyperspectral imaging sub-system for separately distributing radiation emanating from the sample on the detector for simultaneous generation of overlay signals associated with different wavelengths, in accordance with one or more embodiments of the present disclosure.

FIG. 3 is a conceptual view of a hyperspectral imaging sub-system 302 for separately distributing radiation emanating from the sample 104 on the detector 128 for simultaneous generation of overlay signals associated with different wavelengths, in accordance with one or more embodiments of the present disclosure.

In one embodiment, the hyperspectral imaging sub-system 302 includes a dispersive element 304 located at a pupil plane 306 of the overlay metrology tool 102 (e.g., within the collection pathway 132) to spectrally disperse sample radiation 130. For example, the dispersive element 304 may disperse the sample radiation 130 at the pupil plane 306 such that the exit angle of sample radiation 130 from the dispersive element 304 varies according to spectral content (e.g., wavelength). By way of illustration, as shown in FIG. 3, sample radiation 130 including three distinct wavelengths incident on the dispersive element 304 may be dispersed into distinct sub-beams of sample radiation 130 (e.g., $\lambda_1, \lambda_2, \lambda_3$). It is noted, however, that the depiction of sub-beams associated with distinct wavelengths illustrated in FIG. 3 and described above is provided solely for illustrative purposes and should not be interpreted as limiting. For example, the sample radiation 130 may include a broad spectral range (e.g., associated with the spectral range of the illumination beam 114, or the like) such that the sample radiation 130 dispersed by the dispersive element 304 may include a single spectrally-dispersed beam (e.g., without distinct sub-beams).

The dispersive element 304 may be any type of dispersive element known in the art suitable for introducing spectral dispersion into the sample radiation 130. The dispersive element 304 may further introduce dispersion into the sample radiation 130 through any mechanism such as, but not limited to, diffraction or refraction. Further, the dispersive element 304 may be formed from transmissive and/or reflective optical elements. For example, the dispersive element 304 may include, but is not limited to, a diffraction grating or a prism.

In another embodiment, the hyperspectral imaging sub-system 302 includes hyperspectral relay optical elements 308 to relay the pupil plane 306 (e.g., relay an image of the pupil plane 306 located at the first optical element of the hyperspectral imaging sub-system 302, the entrance pupil of the hyperspectral imaging sub-system 302, or the like). For example, as illustrated in FIG. 3, the hyperspectral relay optical elements 308 may collect at least a portion of the spectrally-dispersed sample radiation 130 directed from the dispersive element 304 to form the relayed image of the pupil plane 306. In this regard, the hyperspectral relay optical elements 308 may combine the spectrally-dispersed components of the sample radiation 130 to form the image of the pupil plane 306. Accordingly, the sample radiation 130 may not be spectrally dispersed at the location of the relayed image of the pupil plane 306, but may be spectrally dispersed elsewhere within the hyperspectral imaging sub-system 302.

In another embodiment, the hyperspectral imaging sub-system 302 includes a lens array 310 formed as an array of focusing elements (e.g., lenses). In another embodiment, the lens array 310 is located at the relayed image of the pupil plane 306 such that the lens array 310 divides the sample radiation 130 in the pupil plane 306 into multiple segments according to the distribution of focusing elements of the lens array 310. In this regard, each focusing element of the lens array 310 may capture a particular portion of the distribution of sample radiation 130 in the pupil plane 306.

Accordingly, sample radiation 130 in the pupil plane 306 associated with different wavelengths of the illumination beam 114 may be separately provided to the detector 128. The detector 128 may thus separately and simultaneously provide overlay signals associated with the different wavelengths (e.g., associated with different overlay recipes) to the controller 106.

In another embodiment, an overlay recipe includes a selected angular distribution of the illumination beam 114 on the sample 104. Accordingly, the controller 106 may be communicatively coupled to the illumination source 112 and/or one or more components of the illumination pathway 118 to adjust the angular distribution of the illumination beam 114 on the sample 104.

The angular distribution of the illumination beam 114 on the sample 104 may be adjusted by any optical element or combination of elements suitable for directing the illumination beam 114.

For example, as illustrated in FIG. 1C, the illumination pathway 118 of the overlay metrology tool 102 may include, but is not required to include, a first focusing element 138 positioned at an angle to the sample 104. Further, the first focusing element 138 as well as one or more additional optical components in the illumination pathway 118 may be secured to a rotatable arm (not shown) suitable for controlling the angle at which the illumination beam 114 is incident on the sample. Accordingly, the controller 106 may be communicatively coupled to the rotatable arm such that the controller may direct the rotatable arm to position the illumination beam 114 at a selected angle corresponding to a selected overlay recipe.

Referring now to FIG. 1B, by way of another example, the angle of the illumination beam 114 on the sample 104 may be adjusted within the numerical aperture of the objective lens 124 positioned normal to the sample 104 by positioning and/or shaping the illumination beam 114 in an illumination pupil plane (e.g., a pupil plane in the illumination pathway 118 conjugate to the back focal plane of the objective lens 124).

Figure 4:
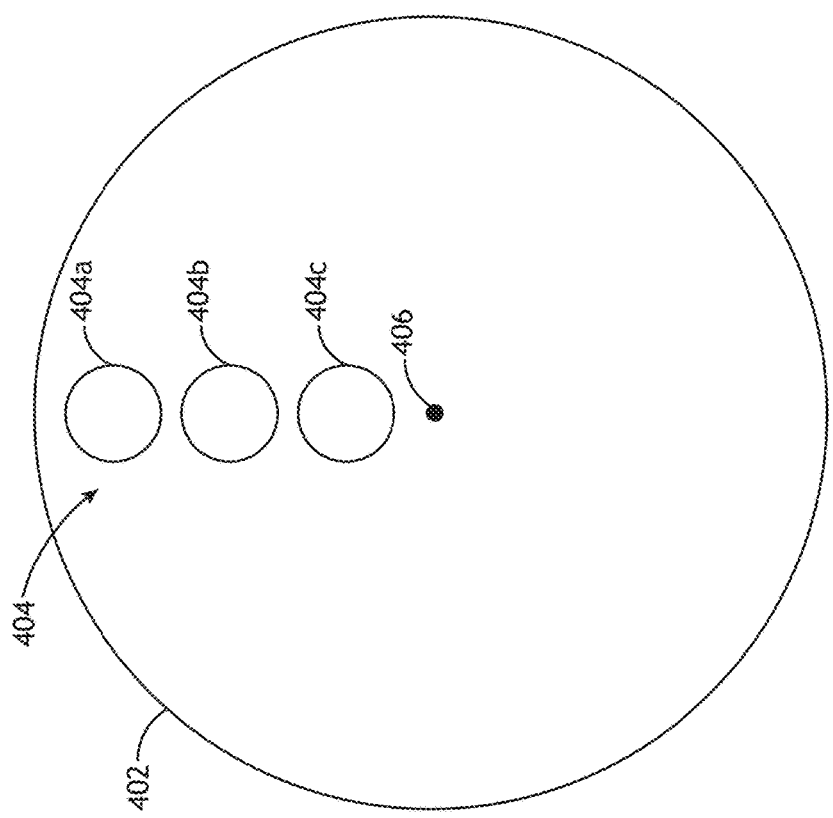
FIG. 4 is a conceptual view of an illumination pupil plane suitable for controlling the angle of incidence of an illumination beam on a sample, in accordance with one or more embodiments of the present disclosure.

FIG. 4 is a conceptual view of an illumination pupil plane 402 suitable for controlling the angle of incidence of an illumination beam 114 on a sample 104, in accordance with one or more embodiments of the present disclosure. In one embodiment, one or more apertures 404 may be positioned away from the optical axis 406 of the illumination pathway 118 in the illumination pupil plane 402. For example, the apertures 404$a,b,c$ may be centered at three off-axis locations in the Z-direction within the illumination pupil plane 402. In this regard, an illumination beam 114 at the illumination pupil plane 402 (e.g., filling at least a portion of the illumination pupil plane 402) may provide the illumination beam 114 on the sample at a selected angle by propagating through any of apertures 404$a,b,c$. Accordingly, off-axis illumination in the illumination pupil plane 402 (e.g., in the Z-direction of FIG. 4) may result in illumination of the sample 104 at an off-normal angle (e.g., <90° in the X-direction of FIG. 1B).

In this regard, the controller 106 communicatively coupled to the apertures 404$a,b,c$ may selectively open a desired aperture to achieve a desired angle of illumination on the sample 104. It is to be understood that the illustration of three apertures (e.g., apertures 404$a,b,c$) in FIG. 4 and the associated description above is provided solely for illustrative purposes and should not be interpreted as limiting. The overlay metrology tool 102 may include any number of apertures having any size, shape, or distribution throughout the illumination pupil plane 402 to provide a desired number of available illumination angles as measurement parameters in overlay recipes. In another embodiment, the controller 106 may direct two or more apertures 404 to open simultaneously to provide simultaneous illumination of the sample 104 and multiple angles of illumination in accordance with multiple overlay recipes.

In another embodiment, the overlay metrology tool 102 may include one or more apodizers to shape the angular distribution on the sample 104 (e.g., the relative intensity of the illumination beam 114 as a function of angle on the sample 104).

In another embodiment, the overlay metrology tool 102 may include one or more elements to shape and/or position the illumination beam 114 at any position in the illumination pupil plane 402. For example, the illumination pathway 118 may include a beam reducer/expander communicatively coupled to the controller 106 to selectively control the diameter of the illumination beam 114. Further, the illumination pathway 118 may include an adjustable beam-control device (e.g., translatable mirrors, tiltable mirrors, prisms, or the like) communicatively coupled to the controller 106 to selectively adjust the position of the illumination beam 114. It is recognized herein that apertures 404 in the illumination pupil plane 402 may block a substantial portion of the power of the illumination beam 114 and may thus increase the power requirements for an illumination beam 114 relative to an unapertured beam to achieve a desired performance specification. Accordingly, shaping and/or positioning the entire illumination beam 114 at a selected position (e.g., an off-axis position or an on-axis position) in the illumination pupil plane 402 may facilitate the use of all of the available power of the illumination beam 114 at any desired illumination angle, which may provide efficient use of the spectral power of the illumination source 112. In another embodiment, the adjustable beam-control device may split an incident illumination beam 114 from the illumination source 112 into two or more sub-beams. The adjustable beam-control device may further adjust the beam diameter and location within the illumination pupil plane 402 of the two or more sub-beams to simultaneously provide multiple angles of illumination on the sample 104 associated with multiple overlay recipes.

In another embodiment, an overlay recipe includes a selected polarization of the illumination beam 114 on the sample 104. Accordingly, the controller 106 may be communicatively coupled to an adjustable polarizer in the illumination pathway 118 to selectively control the polarization of the illumination beam 114 on the sample 104. For example, the adjustable polarizer may include, but is not limited to, a static polarizer in a rotatable translation stage, a Pockels cell, or a liquid crystal device.

In another embodiment, an overlay recipe includes a selected position of the illumination beam 114 on the sample 104. Accordingly, the controller 106 may be communicatively coupled to a beam-scanning device in the illumination pathway 118 to selectively control the location of the illumination beam 114 on the sample 104. For example, the beam-scanning device may move the illumination beam 114 within the bounds of an overlay target on the sample 104 at a rate faster than an integration time of the detector 128 to provide a spatially-averaged overlay signal, which may mitigate artifacts associated with imperfections in the overlay target as well as coherence effects. In one embodiment, the beam-scanning device includes a resonant mirror such as, but not limited to, a micro-electromechanical mirror (MEM) with a resonant frequency higher than the frame rate of the detector 128. For example, a resonant mirror with a resonance of 25 kHz may provide motion of the illumination beam 114 within the overlay target suitable for generating a spatially-averaged overlay signal in less than 0.15 milliseconds.

In another embodiment, an overlay recipe includes a selected position of the sample 104 within a focal volume of the overlay metrology tool 102 (e.g., of the objective lens 124 or the first focusing element 138). Accordingly, the controller 106 may be communicatively coupled to the sample stage 126 to selectively adjust the focal position of the sample 104. For example, the sample stage 126 may include, but is not limited to, one or more translational stages suitable for selectably translating the sample 104 along one or more linear directions (e.g., x-direction, y-direction and/or z-direction). By way of another example, the sample stage 126 may include, but is not limited to, one or more rotational stages suitable for selectably rotating the sample 104 along a rotational direction. By way of another example, the sample stage 126 may include, but is not limited to, a rotational stage and a translational stage suitable for selectably translating the sample along a linear direction and/or rotating the sample 104 along a rotational direction.

Further, any components of the overlay metrology tool 102 may be selectively adjusted to facilitate the rapid tuning of measurement parameters of an overlay recipe and/or the rapid acquisition of overlay signals. For example, an overlay recipe may include one or more acquisition parameters of the detector 128 such as, but not limited to, the integration time, the frame rate, or the gain.

The detector 128 may include any optical detector known in the art suitable for measuring illumination received from the sample 104. For example, a detector 128 may include, but is not limited to, a charge-coupled device (CCD) detector, a complementary metal-oxide-semiconductor (CMOS) detector, a time delay and integration (TDI) detector, a photomultiplier tube (PMT), an avalanche photodiode (APD), or the like. In another embodiment, a detector 128 may include a spectroscopic detector suitable for identifying wavelengths of radiation emanating from the sample 104. Further, the overlay metrology tool 102 may include multiple detectors 128 (e.g., associated with multiple beam paths generated by one or more beamsplitters to facilitate the generation of multiple overlay signals by the overlay metrology tool 102). In one embodiment, the detector 128 includes a high-speed camera (e.g., a Dimax-series camera from PCO AG) suitable for capturing images at a frame rate greater than 1000 frames per second. Accordingly, the overlay metrology tool 102 may, but is not required to, acquire an overlay signal with different recipe every 0.3 milliseconds.

Figure 5:
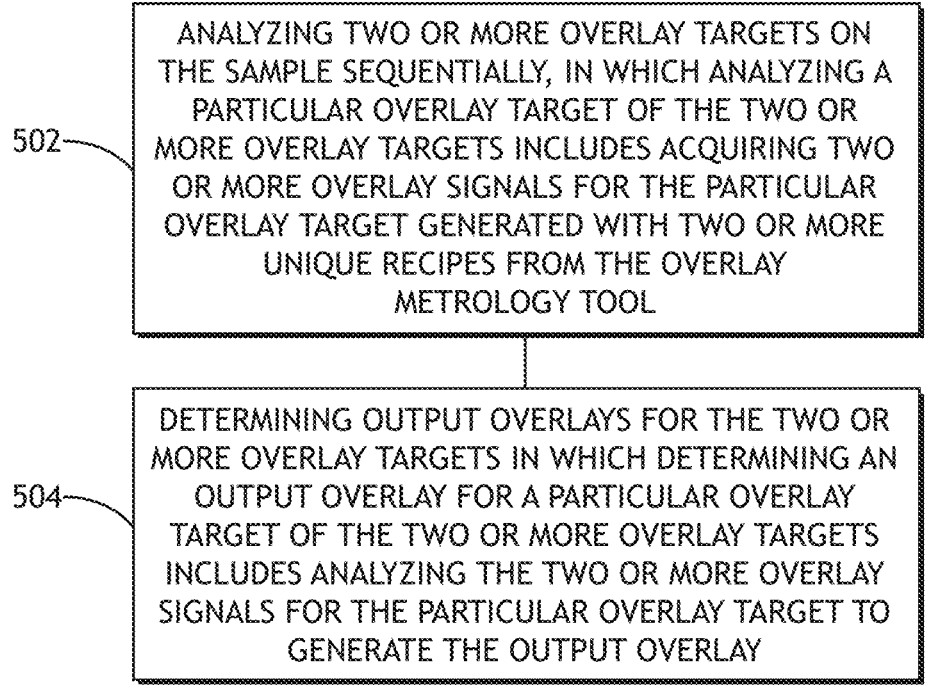
FIG. 5 is a flow diagram illustrating steps performed in a method for determining overlay, in accordance with one or more embodiments of the present disclosure.

FIG. 5 is a flow diagram illustrating steps performed in a method 500 for determining overlay, in accordance with one or more embodiments of the present disclosure. Applicant notes that the embodiments and enabling technologies described previously herein in the context of overlay metrology system 100 should be interpreted to extend to method 500. It is further noted, however, that the method 500 is not limited to the architecture of overlay metrology system 100.

Each of the steps of the method 500 may be performed as described further herein. The steps may be performed by one or more controllers (e.g., controller 106, or the like), which may be configured according to any of the embodiments described herein. In addition, the method described above may be performed by any of the system embodiments described herein. The method 500 may also include one or more additional steps that may be performed by controller or any system embodiments described herein.

In one embodiment, method 500 includes a step 502 of characterizing two or more overlay targets on a sample sequentially in which characterizing a particular overlay target of the two or more overlay targets includes acquiring two or more overlay signals for the particular overlay target generated with two or more unique recipes from the overlay metrology tool. For example, a sample may include a multitude of distributed overlay targets to provide fixed locations at which overlay of two or more sample layers may be measured. For instance, overlay targets may be located in portions of dies on the sample not utilized for device structures or between dies. However, it may be the case that a fixed set of measurement parameters (e.g., a fixed overlay recipe) may not provide the same level of overlay accuracy and repeatability at all locations of the sample due to process variations on the sample (e.g., variations of thicknesses of one or more layers, or variations of the size and/or distribution of overlay target features on one or more sample layers).

Accordingly, step 502 may thus include acquiring two or more overlay signals from an overlay metrology tool (e.g., overlay metrology tool 102) using two or more different recipes. For example, a given overlay recipe may include, but is not required to include or limited to, a selected set of wavelengths of illumination incident on the overlay target, a selected set of measured wavelengths of radiation emanating from the metrology target in response to the incident illumination, a selected set of incident angles of illumination on the sample, a selected polarization of incident illumination, a selected position of the incident illumination on the overlay target, or a selected location of the sample within the focal volume of the overlay metrology tool.

The two or more overlay signals associated with an overlay target generated using the two or more overlay recipes may be acquired sequentially or simultaneously prior to acquiring overlay signals for a subsequent target. For example, the two or more overlay signals may be acquired sequentially by configuring the overlay metrology tool for a first recipe, acquiring a first overlay signal using the first recipe, tuning the overlay metrology tool to use a second recipe, acquiring a second overlay signal using the second recipe, and so on.

In one embodiment, one or more elements of the overlay metrology tool are configured to provide rapid tuning of the overlay metrology tool for rapid acquisition of multiple overlay signals with different recipes. Considering wavelength as an exemplary measurement parameter of an overlay recipe, the overlay metrology tool may include a wavelength selection device such as, but not limited to, tunable edge filters, an acousto-optic double monochromator, a multi-channel spectral filter, or the like suitable for rapidly tuning one or more spectral characteristics of illumination on the sample (e.g., wavelength, bandwidth, spectral profile, or the like). In this regard, the overlay metrology tool may efficiently switch between multiple recipes. In one instance, the overlay metrology tool may be configurable to switch between selected overlay recipes in less than 0.5 milliseconds.

By way of another example, still considering wavelength as an exemplary measurement parameter of an overlay recipe, the overlay metrology tool may include a spectrometer or a hyperspectral detection system to simultaneously detect one or more overlay signals associated with radiation emanating from the sample in response to multiple selected wavelengths of incident illumination. Accordingly, the acquisition time of the multiple simultaneous overlay signals may be equal to the capture time of the detector.

In another embodiment, one or more elements of the overlay metrology tool are configured to provide rapid acquisition of overlay signals with a given recipe. For example, the overlay metrology tool may include a high-speed camera to capture radiation emanating from the sample with a low capture time (e.g., less than 0.5 milliseconds).

Once all overlay signals for a particular overlay target have been acquired, whether sequentially or simultaneously, the step 502 may include aligning the overlay metrology tool to a second overlay target and repeating the process to generate overlay signals for the second overlay target.

In another embodiment, method 500 includes a step 504 of determining output overlays for the two or more overlay targets in which determining an output overlay for a particular overlay target of the two or more overlay targets includes analyzing the two or more overlay signals for the particular overlay target to generate the output overlay.

In one embodiment, the output overlay for an overlay target (e.g., any of the two or more overlay targets) may be determined by generating two or more candidate overlays based on the two or more corresponding overlay signals for that overlay target. For example, each overlay signal from the overlay metrology tool may contain sufficient information to generate a candidate overlay for the corresponding overlay target (e.g., a measurement of the relative positions of two or more layers of the sample at the first overlay target).

In another embodiment, the output overlay for an overlay target may be determined by selecting a single candidate overlay as the output overlay for that overlay target. For example, it may be the case that the two or more candidate overlays generated with differing overlay recipes may not be equal. Accordingly, the step 504 may include determining a relative accuracy and/or repeatability of the two or more candidate overlays. Accordingly, in the case that a given candidate overlay is determined to have an accuracy and/or a repeatability within a selected tolerance, this candidate overlay may be selected as the output overlay associated with the first overlay target.

It is recognized herein that the relative accuracy and/or repeatability of the two or more candidate overlay may be determined in a variety of ways. For example, in an image-based overlay metrology tool in which the overlay signals include images of overlay target features on two or more levels of the sample, the images of the overlay target features may be analyzed and/or ranked according to image quality metrics (e.g., sharpness of focus, contrast, brightness, the presence of image artifacts, or the like).

By way of another example, in a scatterometry-based overlay metrology tool in which the overlay signals include pupil images representative of the angular distribution of radiation from the sample, the pupil images may be analyzed and/or ranked based on the presence or lack of pupil features. For instance, pupil images may be analyzed and/or ranked based on the strength of a 0-order signal in a pupil with respect to one or more higher-order signals. In another instance, the pupil images may be analyzed and/or ranked based on a detected shape of one or more diffraction order signals in the pupil.

In another embodiment, the output overlay for an overlay target may be determined by analyzing the two or more overlay signals for that overlay target in combination. In this regard, the accuracy of the output overlay signal generated based on multiple overlay signals may be improved relative to an output overlay signal generated based on a single overlay signal. For example, eliminating inaccuracy in overlay metrology is generally described in U.S. Patent Publication No. 2016/0313658, titled "Methods of Analyzing and Utilizing Landscapes to Reduce or Eliminate Inaccuracy in Overlay Optical Metrology" and published on Oct. 27, 2016, which is incorporated herein by reference in its entirety.

The determination of an output overlay in step 504 for the two or more overlay targets may be carried out at any time with respect to the acquisition of overlay signals in step 502. In one embodiment, an output overlay for each overlay target is generated sequentially. For example, an overlay metrology system may be aligned to a first overlay target, acquire two or more overlay signals for the first overlay target (e.g., in step 502), and determine an output overlay for the first overlay target based on the two or more overlay signals (e.g., in step 504). Subsequently, the overlay metrology system may be aligned to a second overlay target, acquire two or more overlay signals for the second overlay target (e.g., in step 502), and determine an output overlay for the second overlay target based on the two or more overlay signals (e.g., in step 504). In another embodiment, an overlay metrology system may acquire two or more overlay signals for a first overlay target (e.g., in step 502) and subsequently acquire two or more overlay signals for a second overlay target (e.g., in step 502). However, the determination of output overlay signals (e.g., in step 504) may be performed simultaneously for the first and second overlay targets. Further, the two or more overlay signals associated with each overlay target may be stored in a volatile or a non-volatile memory device prior and processed at any desired time. In this regard, computational time associated with determining output overlays from the overlay signals may not impact the acquisition time of overlay signals on a sample.

In another embodiment, the method 500 may include generating one or more correctables (e.g., correction factors) to be used by process tools (e.g., lithography tools) to fabricate additional layers on the sample based on any overlay errors associated with the output overlays determined in step 504.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected" or "coupled" to each other to achieve the desired functionality, and any two components capable of being so associated can also be viewed as being "couplable" to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. An overlay metrology system, comprising:
   an overlay metrology tool, the overlay metrology tool configurable to generate overlay signals with a plurality of recipes, wherein an overlay signal generated with a particular recipe of the plurality of recipes is suitable for determining overlay of two or more layers of a sample, wherein the overlay metrology tool directs at least a portion of an illumination beam from an illumination source to an overlay target on the sample and collects radiation emanating from the overlay target in response to the at least a portion of the illumination beam to generate the overlay signal with the particular recipe; and
   a controller communicatively coupled to the overlay metrology tool, the controller including one or more processors configured to execute instructions configured to cause the one or more processors to:
      sequentially characterize two or more overlay targets on the sample, wherein characterizing a particular overlay target of the two or more overlay targets includes acquiring two or more overlay signals for the particular overlay target generated with two or more unique recipes from the overlay metrology tool; and determine output overlays for the two or more overlay targets, wherein determining an output overlay for a particular overlay target of the two or more overlay targets includes analyzing the two or more overlay signals for the particular overlay target to generate the output overlay.

2. The overlay metrology system of claim 1, wherein analyzing the two or more overlay signals for the particular overlay target to generate the output overlay comprises:

generating two or more candidate overlays based on the two or more overlay signals for the particular overlay target; and selecting one of the two or more candidate overlays as the output overlay for the particular overlay target.

3. The overlay metrology system of claim 1, wherein analyzing the two or more overlay signals for the particular overlay target to generate the output overlay comprises:

analyzing the two or more overlay signals for the particular overlay target in combination to generating the output overlay.

4. The overlay metrology system of claim 1, wherein the overlay metrology tool sequentially generates the two or more overlay signals for the particular overlay target with the two or more unique recipes.

5. The overlay metrology system of claim 1, wherein the overlay metrology tool tunes to the particular recipe and generates overlay signal with the particular recipe in less or equal to approximately 0.5 milliseconds.

6. The overlay metrology system of claim 1, wherein the overlay metrology tool tunes to the particular recipe and generates overlay signal with the particular recipe in less or equal to approximately 0.3 milliseconds.

7. The overlay metrology system of claim 1, wherein the overlay metrology tool tunes to the particular recipe and generates overlay signal with the particular recipe in less or equal to approximately 0.1 milliseconds.

8. The overlay metrology system of claim 1, wherein the overlay metrology tool simultaneously generates the two or more overlay signals for the particular overlay target with the two or more unique recipes.

9. The overlay metrology system of claim 1, wherein the two or more unique recipes include two or more selected wavelengths from the illumination beam.

10. The overlay metrology system of claim 9, wherein the illumination source is a broadband illumination source, wherein the overlay metrology system further comprises:

a wavelength selection device to filter the spectrum of the illumination beam to sequentially provide the two or more selected wavelengths from the illumination beam.

11. The overlay metrology system of claim 10, wherein the wavelength selection device comprises:

a first tunable dispersive element, wherein a dispersion of the first tunable dispersive element is adjustable, wherein the first tunable dispersive element is configured to introduce spectral dispersion to the illumination beam from the broadband illumination source;

a first optical element, the first optical element configured to receive the illumination beam from the first tunable dispersive element and focus the illumination beam at a focal plane, wherein a spatial distribution of a spectrum of the illumination beam at the focal plane is controllable by adjusting the dispersion of the first tunable dispersive element;

a spatial filtering element located at the focal plane, wherein the spatial filtering element filters a spectrum of the illumination beam based on the spatial distribution of the spectrum of the illumination beam at the focal plane;

a second optical element configured to collect the illumination beam having a filtered spectrum from the spatial filtering element; and a second tunable dispersive element configured to receive the illumination beam from the second optical element, wherein a dispersion of the second tunable dispersive element is configured to correspond to the dispersion of the first tunable dispersive element, wherein the second tunable dispersive element is configured to remove the spectral dispersion introduced by the first tunable dispersive element from the illumination beam, wherein the controller is communicatively coupled to the first tunable dispersive element and the second tunable dispersive element to control the dispersion of the first tunable dispersion element and the second tunable dispersive element to select the wavelength of the illumination beam.

12. The overlay metrology system of claim 10, wherein the wavelength selection device comprises:

two or more filtering channels including two or more channel beam paths, wherein the two or more filtering channels are configured to filter illumination propagating along the two or more channel beam paths based on two or more spectral transmissivity distributions;

a channel selector configured to direct at least a portion of the illumination beam from the broadband illumination source into at least one selected filtering channel of the two or more filtering channels to filter the at least a portion of the illumination beam based on a selected spectral transmissivity distribution of the two or more spectral transmissivity distributions; and at least one beam combiner to combine illumination from the two or more filtering channels to a single output illumination beam, wherein the controller is communicatively coupled to the channel selector to select the at least one selected filtering channel to select the wavelength of the illumination beam.

13. The overlay metrology system of claim 9, wherein the illumination beam from the illumination source includes the two or more selected wavelengths associated with the two or more recipes, wherein the overlay metrology tool simultaneously generates the two or more overlay signals based on the radiation emanating from the sample associated with the two or more selected wavelengths.

14. The overlay metrology system of claim 13, wherein the overlay metrology tool comprises:

one or more illumination optical elements configured to direct the illumination beam including the two or more selected wavelengths to the sample;

one or more collection optical elements configured to collect radiation emanating from the sample;

a detector; and a hyperspectral imaging sub-system, comprising:

a dispersive element positioned at a pupil plane of the set of collection optics configured to spectrally disperse the collected radiation, wherein the collected radiation associated with the two or more selected wavelengths propagate along separate paths;

a lens array including an array of focusing elements; and one or more imaging optics, wherein the one or more imaging optics combine the spectrally-dispersed collected radiation associated with the two or more selected wavelengths to form an image of the pupil plane on the lens array, wherein the focusing elements of the lens array distribute the collected radiation on the detector in an arrayed pattern with the collected radiation associated with the two or more selected wavelengths spatially separated on the detector, wherein the detector simultaneously generates the two or more overlay signals.

15. The overlay metrology system of claim 1, wherein the two or more recipes include two or more angular distributions of illumination on the sample.

16. The overlay metrology system of claim 15, wherein the overlay metrology tool includes one or more adjustable apertures located in an illumination pupil plane configured to transmit a selected portion of the illumination beam to provide a selected angular distribution of the illumination beam on the sample, wherein the controller is communicatively coupled to the one or more adjustable apertures to control the angular distribution of illumination on the sample.

17. The overlay metrology system of claim 15, wherein the overlay metrology tool includes a beam-control device to adjust a position of the illumination beam in an illumination pupil plane to provide a selected angular distribution of the illumination beam on the sample, wherein the controller is communicatively coupled to the beam-control device to control the angular distribution of illumination on the sample.

18. The overlay metrology system of claim 17, wherein the beam-control device splits the illumination beam into two or more sub-beams having diameters smaller than the illumination pupil plane and adjusts positions of the two or more sub-beams in the illumination pupil plane to simultaneously provide multiple selected angular distributions of the illumination beam on the sample.

19. The overlay metrology system of claim 1, wherein the two or more recipes include two or more polarizations of illumination on the sample, wherein the overlay metrology tool includes an adjustable polarizer configured to control the polarization of illumination on the sample, wherein the controller is communicatively coupled to the adjustable polarizer to control the polarization of illumination on the sample.

20. The overlay metrology system of claim 1, wherein the two or more recipes include two or more positions of the sample in a focal volume of the overlay metrology tool, wherein the overlay metrology tool includes an adjustable stage for securing the sample and configured to control the position of the sample in the focal volume of the overlay metrology tool, wherein the controller is communicatively coupled to the adjustable stage to control the position of the sample in the focal volume of the overlay metrology tool.

21. The overlay metrology system of claim 1, wherein the overlay metrology tool further includes an adjustable beam scanner to modify a position of the at least a portion of the illumination beam on the sample with a rate faster than a framerate of a detector for capturing the radiation emanating from the sample.

22. The overlay metrology system of claim 21, wherein the adjustable beam scanner comprises:
a micro-electromechanical scanning mirror.

23. The overlay metrology system of claim 22, wherein the adjustable beam scanner comprises:
a micro-electromechanical scanning mirror with a resonant frequency of at least 25 kHz.

24. The overlay metrology system of claim 1, wherein the overlay metrology tool is an image-based overlay measurement device, wherein the two or more datasets include two or more images of the overlay target based on illumination with the two or more illumination spectra.

25. The overlay metrology system of claim 1, wherein the overlay metrology tool is a scatterometry-based overlay measurement device, wherein the two or more datasets include two or more measurements of a pupil plane of the overlay measurement device indicative of an angular distribution of radiation emanating from the sample in response to illumination from the broadband illumination source.

26. An overlay metrology system, comprising:
a broadband illumination source configured to generate an illumination beam;
a wavelength selection device to filter the illumination beam to provide a selected wavelength of illumination;
an overlay metrology tool, the overlay metrology tool configurable to generate overlay signals with a plurality of recipes including selected wavelengths from the illumination beam provided by the wavelength selection device, wherein an overlay signal generated with a particular recipe of the plurality of recipes is suitable for determining an overlay measurement for two or more layers of a sample, wherein the overlay metrology tool directs illumination from the wavelength selection device to an overlay target on the sample and collects radiation emanating from the overlay target in response to the at least a portion of an illumination beam from an illumination source to generate the overlay signals; and
a controller communicatively coupled to the wavelength selection device and the overlay metrology tool, the controller including one or more processors configured to execute instructions configured to cause the one or more processors to:
sequentially analyze two or more overlay targets on the sample, wherein analyzing a particular overlay target of the two or more overlay targets includes acquiring two or more overlay signals for the particular overlay target generated with two or more unique recipes from the overlay metrology tool; and
determine output overlays for the two or more overlay targets, wherein determining an output overlay for a particular overlay target of the two or more overlay targets includes analyzing the two or more overlay signals for the particular overlay target to generate the output overlay.

27. The overlay metrology system of claim 26, wherein analyzing the two or more overlay signals for the particular overlay target to generate the output overlay comprises:
generating two or more candidate overlays based on the two or more overlay signals for the particular overlay target; and
selecting one of the two or more candidate overlays as the output overlay for the particular overlay target.

28. The overlay metrology system of claim 26, wherein analyzing the two or more overlay signals for the particular overlay target to generate the output overlay comprises:
analyzing the two or more overlay signals for the particular overlay target in combination to generate the output overlay.

29. The overlay metrology system of claim 26, wherein the wavelength selection device comprises:
a first tunable dispersive element, wherein a dispersion of the first tunable dispersive element is adjustable, wherein the first tunable dispersive element is configured to introduce spectral dispersion to the illumination beam from the broadband illumination source;

a first optical element, the first optical element configured to receive the illumination beam from the first tunable dispersive element and focus the illumination beam at a focal plane, wherein a spatial distribution of a spectrum of the illumination beam at the focal plane is controllable by adjusting the dispersion of the first tunable dispersive element;

a spatial filtering element located at the focal plane, wherein the spatial filtering element filters a spectrum of the illumination beam based on the spatial distribution of the spectrum of the illumination beam at the focal plane;

a second optical element configured to collect the illumination beam having a filtered spectrum from the spatial filtering element; and a second tunable dispersive element configured to receive the illumination beam from the second optical element, wherein a dispersion of the second tunable dispersive element is configured to correspond to the dispersion of the first tunable dispersive element, wherein the second tunable dispersive element is configured to remove the spectral dispersion introduced by the first tunable dispersive element from the illumination beam, wherein the controller is communicatively coupled to the first tunable dispersive element and the second tunable dispersive element to control the dispersion of the first tunable dispersive element and the second tunable dispersive element to select the wavelength of the illumination beam.

30. The overlay metrology system of claim 26, wherein the wavelength selection device comprises:

two or more filtering channels including two or more channel beam paths, wherein the two or more filtering channels are configured to filter illumination propagating along the two or more channel beam paths based on two or more spectral transmissivity distributions;

a channel selector configured to direct at least a portion of the illumination beam from the broadband illumination source into at least one selected filtering channel of the two or more filtering channels to filter the at least a portion of the illumination beam based on a selected spectral transmissivity distribution of the two or more spectral transmissivity distributions; and at least one beam combiner to combine illumination from the two or more filtering channels to a single output illumination beam, wherein the controller is communicatively coupled to the channel selector to select the at least one selected filtering channel to select the wavelength of the illumination beam.

31. The overlay metrology system of claim 26, wherein the two or more recipes include two or more angular distributions of illumination on the sample.

32. The overlay metrology system of claim 31, wherein the overlay metrology tool includes one or more adjustable apertures located in an illumination pupil plane configured to transmit a selected portion of the illumination beam to provide a selected angular distribution of the illumination beam on the sample, wherein the controller is communicatively coupled to the one or more adjustable apertures to control the angular distribution of illumination on the sample.

33. The overlay metrology system of claim 31, wherein the overlay metrology tool includes a beam-control device to adjust a position of the illumination beam in an illumination pupil plane to provide a selected angular distribution of the illumination beam on the sample, wherein the controller is communicatively coupled to the beam-control device to control the angular distribution of illumination on the sample.

34. The overlay metrology system of claim 33, wherein the beam-control device splits the illumination beam into two or more sub-beams having diameters smaller than the illumination pupil plane and adjusts positions of the two or more sub-beams in the illumination pupil plane to simultaneously provide multiple selected angular distributions of the illumination beam on the sample.

35. The overlay metrology system of claim 26, wherein the two or more recipes include two or more polarizations of illumination on the sample, wherein the overlay metrology tool includes an adjustable polarizer configured to control the polarization of illumination on the sample, wherein the controller is communicatively coupled to the adjustable polarizer to control the polarization of illumination on the sample.

36. The overlay metrology system of claim 26, wherein the two or more recipes include two or more positions of the sample in a focal volume of the overlay metrology tool, wherein the overlay metrology tool includes an adjustable stage for securing the sample and configured to control the position of the sample in the focal volume of the overlay metrology tool, wherein the controller is communicatively coupled to the adjustable stage to control the position of the sample in the focal volume of the overlay metrology tool.

37. The overlay metrology system of claim 26, wherein the overlay metrology tool further includes an adjustable beam scanner to modify a position of the at least a portion of the illumination beam on the sample with a rate faster than a framerate of a detector for capturing the radiation emanating from the sample.

38. The overlay metrology system of claim 37, wherein the adjustable beam scanner comprises:

a micro-electro-mechanical scanning mirror.

39. The overlay metrology system of claim 38, wherein the adjustable beam scanner comprises:

a micro-electro-mechanical scanning mirror with a resonant frequency of at least 25 kHz.

40. The overlay metrology system of claim 26, wherein the overlay metrology tool is an image-based overlay measurement device, wherein the two or more datasets include two or more images of the overlay target based on illumination with the two or more illumination spectra.

41. The overlay metrology system of claim 26, wherein the overlay metrology tool is a scatterometry-based overlay measurement device, wherein the two or more datasets include two or more measurements of a pupil plane of the overlay measurement device indicative of an angular distribution of radiation emanating from the sample in response to illumination from the broadband illumination source.

42. An overlay metrology system, comprising:

an overlay metrology tool, the overlay metrology tool configurable to generate overlay signals with a plurality of recipes including selected wavelengths from the illumination beam provided by the wavelength selection device, wherein an overlay signal generated with a particular recipe of the plurality of recipes is suitable for determining an overlay measurement for two or more layers of a sample, the overlay metrology tool comprising:

an illumination source configured to generate an illumination beam including two or more selected wavelengths;

one or more illumination optical elements configured to direct the at least a portion of the illumination beam including the two or more selected wavelengths to the sample;

one or more collection optical elements configured to collect radiation emanating from the sample in response to the at least a portion of the illumination beam including the two or more selected wavelengths; and a hyperspectral detector, the hyperspectral detector configured to simultaneously generate two or more overlay signals associated with the radiation emanating from the sample in response to the two or more selected wavelengths; and a controller communicatively coupled to the wavelength selection device and the overlay metrology tool, the controller including one or more processors configured to execute instructions configured to cause the one or more processors to:

sequentially analyze two or more overlay targets on the sample, wherein analyzing a particular overlay target of the two or more overlay targets includes acquiring two or more overlay signals for the particular overlay target generated with two or more unique recipes from the overlay metrology tool; and determine output overlays for the two or more overlay targets, wherein determining an output overlay for a particular overlay target of the two or more overlay targets includes analyzing the two or more overlay signals for the particular overlay target to generate the output overlay.

43. The overlay metrology system of claim 42, wherein analyzing the two or more overlay signals for the particular overlay target to generate the output overlay comprises:
generating two or more candidate overlays based on the two or more overlay signals for the particular overlay target; and
selecting one of the two or more candidate overlays as the output overlay for the particular overlay target.

44. The overlay metrology system of claim 42, wherein analyzing the two or more overlay signals for the particular overlay target to generate the output overlay comprises:
analyzing the two or more overlay signals for the particular overlay target in combination to generate the output overlay.

45. The overlay metrology system of claim 42, wherein the hyperspectral detector comprises:
a detector;
a dispersive element positioned at a pupil plane of the set of collection optics configured to spectrally disperse the collected radiation, wherein the collected radiation associated with the two or more selected wavelengths propagate along separate paths;
a lens array including an array of focusing elements; and
one or more imaging optics, wherein the one or more imaging optics combine the spectrally-dispersed collected radiation associated with the two or more selected wavelengths to form an image of the pupil plane on the lens array, wherein the focusing elements of the lens array distribute the collected radiation on the detector in an arrayed pattern with the collected radiation associated with the two or more selected wavelengths spatially separated on the detector, wherein the detector simultaneously generates the two or more overlay signals.

46. An overlay measurement method, comprising:
analyzing two or more overlay targets on the sample sequentially, wherein analyzing a particular overlay target of the two or more overlay targets includes acquiring two or more overlay signals for the particular overlay target generated with two or more unique recipes from the overlay metrology tool; and
determining output overlays for the two or more overlay targets, wherein determining an output overlay for a particular overlay target of the two or more overlay targets includes analyzing the two or more overlay signals for the particular overlay target to generate the output overlay.

47. The overlay measurement method of claim 46, wherein analyzing the two or more overlay signals for the particular overlay target to generate the output overlay comprises:
generating two or more candidate overlays based on the two or more overlay signals for the particular overlay target; and
selecting one of the two or more candidate overlays as the output overlay for the particular overlay target.

48. The overlay measurement method of claim 46, wherein analyzing the two or more overlay signals for the particular overlay target to generate the output overlay comprises:
analyzing the two or more overlay signals for the particular overlay target in combination to generate the output overlay.

49. The overlay measurement method of claim 46, wherein a particular recipe of the two or more unique of recipes comprises:
at least one of a selected wavelength of the at least a portion of the illumination beam on the sample, an angle of incidence of the at least a portion of the illumination beam on the sample, a polarization of the at least a portion of the illumination beam on the sample, a position of the at least a portion of the illumination beam on the sample, or a position of the sample within a focal volume of the overlay metrology tool.

* * * * *